United States Patent [19]

Smith et al.

[11] Patent Number: 5,210,024

[45] Date of Patent: May 11, 1993

[54] ISOLATION OF STRAINS OF SACCHAROMYCES CEREVISIAE HAVING ALTERED ALPHA-ACETYLTRANSFERASE ACTIVITY

[75] Inventors: John A. Smith, Scotch Plains, N.J.; Fang-Jen S. Lee, Bethesda, Md.

[73] Assignee: The General Hospital Corporation, Boston, Mass.

[21] Appl. No.: 803,734

[22] Filed: Dec. 9, 1991

Related U.S. Application Data

[63] Continuation of Ser. No. 426,381, Oct. 25, 1989, which is a continuation-in-part of Ser. No. 284,344, Dec. 14, 1988, Pat. No. 4,966,848, and a continuation-in-part of Ser. No. 153,361, Feb. 8, 1988, abandoned.

[51] Int. Cl.⁵ .................... C12P 21/02; C12N 15/54; C12N 9/10
[52] U.S. Cl. .............................. 435/68.1; 435/240.4; 435/252.3; 435/254; 435/193; 536/23.2
[58] Field of Search .................... 435/68.1, 193, 240.4, 435/252.3, 254; 536/27

[56] References Cited

PUBLICATIONS

Lee, F.-J. S., et al. (1989) *J. Biol. Chem.* 264(21), 12334–12343.
Lee, F.-J. S., et al. (1988) *J. Biol. Chem.* 263(29), 14948–14955.
Suggs, S. V., et al. (1981) *Proc. Natl. Acad. Sci., U.S.A.* 78(11), 6613–6617.
Adelman, J. P., et al. (1983) *DNA* 2(3), 183–193.
Lee, F-J. S. et al., *Febs Lett.* 256:139–142 (1989).
Mullen, J.R. et al., *The EMBO Journal* 8:2067–2075 (1989).
Hartwell, L. H., *Journal of Bacteriology* 93:1662–1670 (1967).
Klyce, H. R. et al., *Experimental Cell Research* 82:47–56 (1973).
Rose, M. D. et al., *Gene* 60:237–243 (1987).
Shore, D. et al., *The EMBO Journal* 3:2817–2823 (1984).
Last, R. L. et al., *Molecular and Cellular Biology* 4:2396–2405 (1984).
Tsunasawa, S. et al., *Methods In Enzymology* 106:165–170 (1984).
Driessen, H. P. C. et al., *CRC Critical Revies in Biochemistry* 18:281–325 (1985).
Hershko, A. et al., *Proc. Nat'l Acad. Sci. USA* 81:7021–7025 (1984).
Bachmair, A. et al., *Science* 234:179–186 (1986).
Brown, J. L., *Int'l Congr. Biochem. (Int'l Union of Biochem., Canada)* Abstracts 11:90 (1979).
Lee, F. J. S. et al., *Journal of Bacteriology* 171:5795–5802 (1989).
Travis, G. H. et al., *The Journal of Biological Chemistry* 259:14406–14412 (1984).
Rothstein, R.J., *Methods in Enzymology* 101:202–211 (1983).
Haywood, G. W. et al., *Eur. J. Biochem.* 148:277–283 (1985).
Strauch, E. et al., *Gene* 63:65–74 (1988).

*Primary Examiner*—Charles L. Patterson, Jr.

[57] ABSTRACT

A mutation defining a gene for the $N^{\alpha}$-acetyltransferase of yeast has been identified and cloned. Mutations in this gene have been constructed and used to produce cells which are substantially incapable of catalyzing $N^{\alpha}$-acetylation of protein. Such cells are valuable tools for determining the amino acid sequence of uncharacterized proteins. Such cells are also valuable tools for expressing a recombinant protein lacking an acetyl group at its α-amino group.

8 Claims, 6 Drawing Sheets

FIG. 1A

```
5'.....TTTCCAGGACCCTAACGAAGT

22  ATG TCT AGG AAA AGA AGT ACT AAG CCC AAG CCA GCA GCT TTG AAA AAA GAA AAT GAC CAG
  1   M   S   R   K   R   S   T   K   P   K   P   A   A   L   K   K   E   N   D   Q

91  TTC CTC GAG GCA TTG AAA CTA TAC GAA GGG AAG CAA TAC CTC AAG CTG CTA GAC GCA ATT
 24   F   L   E   A   L   K   L   Y   E   G   K   Q   Y   L   K   L   L   D   A   I

160  TTG AAA AAA GAC GGT AGT CAC GTT GAT TCC GCT TTA AAG AAA TCT CTC GTA TAT TCT GTA GGT GAG
 47   L   K   K   D   G   S   H   V   D   S   A   L   K   K   S   L   Y   S   V   G   E

229  AAA GAT GAC GCT GCT TCC TAC GTG GTA GCT AAT GCC ATC AGA AAA ATT GAA GGC GCT TCA GCA TCA CCA ATC
 70   K   D   D   A   A   S   Y   V   V   A   N   A   I   R   K   I   E   G   A   S   P   I
           ---25-2---                              ---27-3---

298  TGC TGT CAT GTA TTA TTA GGT TAT ATC TAC ATG AGA AGA AAC ACC AAA GAG TAC AAA GAA TCT ATT AAA TGG TTC ACG
 93   C   C   H   V   L   L   G   Y   I   Y   M   R   R   N   T   K   E   Y   K   E   S   I   K   W   F   T

367  GCA GCT TTG AAC AAT GGG TCC ACT AAC AAG CAA ATA TAT AGA GAC TTA GCA ACT TTG CAA TCA CAA ATT
116   A   A   L   N   N   G   S   T   N   K   Q   I   Y   R   D   L   A   T   L   Q   S   Q   I
                                                                         ---20-4---

436  GGC GAT TTC AAA AAT GCT CTT GTG TCC AGG AAA CAA GAT GTG AAC GGT GAG TTC CTT GGT TAC CGT GCC AAC
139   G   D   F   K   N   A   L   V   S   R   K   Q   D   V   N   G   E   F   L   G   Y   R   A   N
                                                                 ---28-2---

505  TGG ACA TCA TTG ACA GCT GTG GCA CAA GAT GAT AAA ATA TCT GAT GAG AGG AGG CAA CAA GCT ATT AAC ACT TTA TCT CAG
162   W   T   S   L   T   A   V   A   Q   D   D   K   I   S   D   E   R   R   Q   Q   A   I   N   T   L   S   Q

574  TTT GAA AAA CTC GCT GAG GGA AAA ATA ATG TAT AAA AAG TAT GAA AAA TAT GAA CAC AGC GAG TGT TTA ATG TAC
185   F   E   K   L   A   E   G   K   I   M   Y   K   K   Y   E   K   Y   E   H   S   E   C   L   M   Y

643  AAA AAC GAC ATT ATG TAT AAA GCT GCC AGT GAT AAC CAA GAC AAG TTA CAA AAT GTA TTG AAA CAT TTG
208   K   N   D   I   M   Y   K   A   A   S   D   N   Q   D   K   L   Q   N   V   L   K   H   L
```

```
712   AAT GAT ATC GAG CCA TGC GTC TTT GAT AAA TTT GGT TTA TTA GAG AGA AAA GCA ACT ATT TAC ATG AAA
231    N   D   I   E   P   C   V   F   D   K   F   G   L   L   E   R   K   A   T   I   Y   M   K

781   TTG GGT CAA TTG CAA GAC GCG TCC ATT GTT TAT AGA ACT CTG ATC AAG AGA AAT CCA GAT AAT TTT AAG
254    L   G   Q   L   Q   D   A   S   I   V   Y   R   T   L   I   K   R   N   P   D   N   F   K

850   TAC TAC AAA TTA CTC GAA GTA TCC TTG GGA ATC CAA GGT GAC AAT AAA TTG AAG AAG GCT TTG TAT GGA
277    Y   Y   K   L   L   E   V   S   L   G   I   Q   G   D   N   K   L   K   K   A   L   Y   G

919   AAA CTT GAA CAA TTT TAT CCA AGA TGC GAA CCA CCC AAA TTT ATT CCA TTA ACT TTC CTT CAA GAC AAA
300    K   L   E   Q   F   Y   P   R   C   E   P   P   K   F   I   P   L   T   F   L   Q   D   K

988   GAA GAG CTC AGC AAA AAA TTG AGA GAA TAT GTT TTG CCT CAA TTG GAG CGC GGT GTT CCA GCA ACT TTT
323    E   E   L   S   K   K   L   R   E   Y   V   L   P   Q   L   E   R   G   V   P   A   T   F

1057  TCC AAC GTG CTC AAA CCC CTT TAC CAA AGA AAG TCC AAG GTT TCA CCA CTA TTG GAG AAA ATT GTC CTT
346    S   N   V   L   K   P   L   Y   Q   R   K   S   K   V   S   P   L   L   E   K   I   V   L

1126  GAT TAT TTG TCC GGA TTA GAT CCT ACG CAG GAT CCA ATT CCT TTT ATT TGG ACC AAT TAT TAC TTG TCT
369    D   Y   L   S   G   L   D   P   T   Q   D   P   I   P   F   I   W   T   N   Y   Y   L   S

1195  CAA CAT TTC CTT TTC CTT AAG GAT TTT CCG AAA GCC CAA GAA TAT ATT GAT GCT GCC CTT GAC CAC ACC
392    Q   H   F   L   F   L   K   D   F   P   K   A   Q   E   Y   I   D   A   A   L   D   H   T

1264  CCA ACT TTA GTT GAG TTT TAC ATC CTC AAG GCA CGT ATC CTG AAG CAC CTA GGC CTA ATG GAC ACA GCG
415    P   T   L   V   E   F   Y   I   L   K   A   R   I   L   K   H   L   G   L   M   D   T   A
```

FIG. 1B

```
1333  GCT GGA ATT TTG GAG GAA GGT AGG CAA CTT GAT AGA TTT ATC AAC TGT AAA ACG GTT AAG
 438   A   G   I   L   E   E   G   R   Q   L   D   R   F   I   N   C   T   V   K

1402  TAC TTT TTA AGG GCT AAC AAT ATC GAC AAG GCG GTG GAA GTC GCG TCC CTT TTC ACC AAA AAC GAT GAT
 461   Y   F   L   R   A   N   N   I   D   K   A   V   E   V   A   S   L   F   T   K   N   D   D
                                                                    |---15-1-1---|

1471  TCT GTT AAT GGT ATT AAG GAC CAC CTT TGG TCT GAA GCT CTG GAA GTA ATC GTT TGG TTC GAA CAG GAA GCC
 484   S   V   N   G   I   K   D   H   L   W   S   E   A   L   E   V   I   V   W   F   E   Q   E   A

1540  TAT TAT AGA CTA TAC CTG GAT AGA AAA TTA GAC GAT TTA GCA TCG CTA AAA AAA GAG GTT GAA
 507   Y   Y   R   L   Y   L   D   R   K   L   D   D   L   A   S   L   K   K   E   V   E

1609  AGT GAT AAA AGC GAA CAA ATT GCG AAC GCT ATT CCA ATT AAA GAA CAA CAA TGG CTT GTT CGC AAA TAT AAA GGT
 530   S   D   K   S   E   Q   I   A   N   A   I   P   I   K   E   Q   Q   W   L   V   R   K   Y   K   G

1678  TTG GCC CTG AAA AGA TTC AAC GCT CCA AGA ACG CCA AGA ATG AAG GCA ATG AAG GAA GAT GAC CAG TTG GAT TTC
 553   L   A   L   K   R   F   N   A   P   R   T   P   R   M   K   A   M   K   E   D   D   Q   L   D   F

1747  CAT TCA TAC TGT ATG AGA AAA CGC GGA ATG TAT CTC GAG ATG TTA GAA TGG GGA AAG GCA CTT
 576   H   S   Y   C   M   R   K   G   M   Y   L   E   M   L   E   W   G   K   A   L
                                                   |------27-1------|

1816  TAT ACC AAA CCC ATG TAT GTT CGC GCA ATG AAG GAA GCA TCA AAG CTT TAC TTT CAA ATG CAT GAT GAT
 599   Y   T   K   P   M   Y   V   R   A   M   K   E   A   S   K   L   Y   F   Q   M   H   D   D
              |----9-2-2----|                                        |-------10-3-1-------|

1885  CGC TTA AAA AGA AAG TCC GAT TCT TTA GAT GAA AAT TCA GAT GAA ATC CAA AAT AAT GGC CAA AAT AGT
 622   R   L   K   R   K   S   D   S   L   D   E   N   S   D   E   I   Q   N   N   G   Q   N   S

1954  AGC AGC CAA AAG AAA GCT AAG AAG GAA GCA GCC GCT ATG AAC AAA CGG AAA GAA ACT GAA GCC AAG
 645   S   S   Q   K   K   A   K   K   E   A   A   A   M   N   K   R   K   E   T   E   A   K
```

FIG. 1C

| | | | | | | | | | | | | | | | | | | | | | | |
|---|---|---|---|---|---|---|---|---|---|---|---|---|---|---|---|---|---|---|---|---|---|---|
| 2023<br>668 | AGT<br>S | GTT<br>V | GCT<br>A | GCT<br>A | TAT<br>Y | CCG<br>P | AGT<br>S | GAT<br>D | CAA<br>Q | GAT<br>D | AAC<br>N | GAT<br>D | GTA<br>V | TTC<br>F | GGC<br>G | GAA<br>E | AAG<br>K | TTG<br>L | ATT<br>I | GAA<br>E | ACC<br>T | TCC ACT<br>S T |

←----------------------11-3-2----------------------→

| 2092<br>691 | CCA<br>P | ATG<br>M | GAG<br>E | GAC<br>D | TTC<br>F | GCT<br>A | ACC<br>T | GAA<br>E | TTT<br>F | TAT<br>Y | AAT<br>N | AAC<br>N | TAC<br>Y | TCC<br>S | ATG<br>M | CAA<br>Q | GTC<br>V | AGA<br>R | GAA<br>E | GAC<br>D | AGG<br>R | GAT<br>D |

←------------35-2, 39-1------------→

| 2161<br>714 | TAT<br>Y | ATT<br>I | TTG<br>L | GAC<br>D | TTT<br>F | GAA<br>E | TTT<br>F | AAC<br>N | TAC<br>Y | AGA<br>R | ATT<br>I | GGA<br>G | AAG<br>K | TTA<br>L | GCT<br>A | TTG<br>L | TGC<br>C | TTT<br>F | GCT<br>A | TCT<br>S | CTA<br>L | AAC<br>N | AAA<br>K |
| 2230<br>737 | TTC<br>F | GCT<br>A | AAG<br>K | AGA<br>R | TTT<br>F | GGC<br>G | ACC<br>T | ACG<br>T | AGC<br>S | GGT<br>G | TTA<br>L | TTT<br>F | GGT<br>G | AGT<br>S | ATG<br>M | GCC<br>A | ATT<br>I | GTT<br>V | TTG<br>L | TTA<br>L | CAT<br>H | GCC<br>A | ACA<br>T |
| 2299<br>760 | AGA<br>R | AAC<br>N | GAC<br>D | ACC<br>T | CCC<br>P | TTT<br>F | GAT<br>D | CCA<br>P | ATT<br>I | TTG<br>L | AAG<br>K | AAA<br>K | GTA<br>V | GTC<br>V | ACG<br>T | AAG<br>K | AGC<br>S | CTT<br>L | GAA<br>E | AAA<br>K | GAG<br>E | TAT<br>Y | TCT<br>S |
| 2368<br>783 | GAA<br>E | AAT<br>N | TTC<br>F | CCA<br>P | TTA<br>L | AAC<br>N | GAA<br>E | ATA<br>I | TCT<br>S | AAC<br>N | AAT<br>N | AGC<br>S | TTC<br>F | GAT<br>D | TGG<br>W | CTG<br>L | AAT<br>N | TTC<br>F | TAC<br>Y | CAA<br>Q | GAA<br>E | AAA<br>K | TTC<br>F |
| 2437<br>806 | GGT<br>G | AAG<br>K | AAT<br>N | GAT<br>D | ATA<br>I | AAT<br>N | ATG<br>M | ATT<br>I | ATT<br>I | AGC<br>S | AGT<br>S | CTT<br>L | TTT<br>F | CTG<br>L | CTA<br>L | TTT<br>F | CGC<br>R | TAT<br>Y | CGC<br>R | GAT<br>D | GTT<br>V | CCG<br>P | ATC<br>I | GGA<br>G | AGC<br>S | TCT<br>S |
| 2506<br>829 | AAT<br>N | TTG<br>L | AAA<br>K | GAA<br>E | ATG<br>M | ATT<br>I | ATT<br>I | AGC<br>S | AGT<br>S | CTT<br>L | TCT<br>S | CCC<br>P | TTG<br>L | GAG<br>E | CCT<br>P | CAC<br>H | TCC<br>S | CAG<br>Q | AAC<br>N | GAA<br>E | ATT<br>I | CTA<br>L | CAG<br>Q |
| 2575<br>852 | TAT<br>Y | TAC<br>Y. | TTG<br>L | TAG<br>* | CCTGCAACTCCTCAATGTCTCAATTAACTCTTACTTAATTATGTATATTTTTATGTATATGCTTATATGCA |
| 2662 | TGCGCATATGCTCATAAAGATACATTGTTATAGGTCAAAAAAAAAAAAAAAAAA.....3' |

FIG. 1D

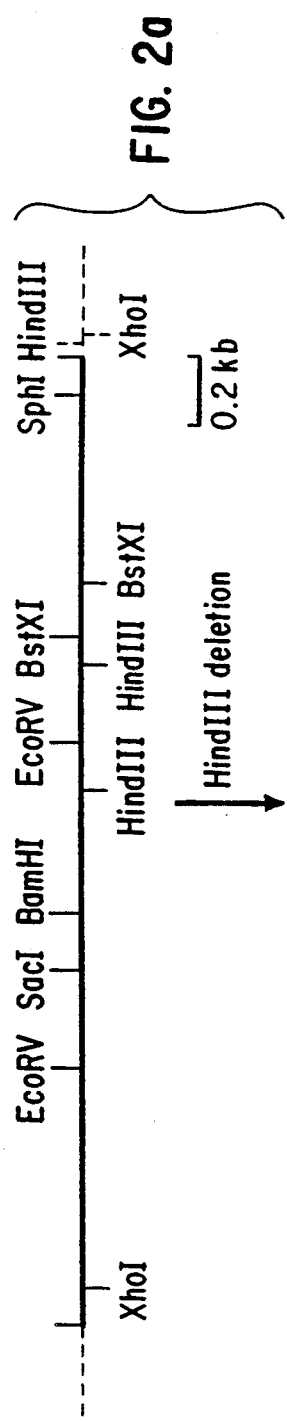
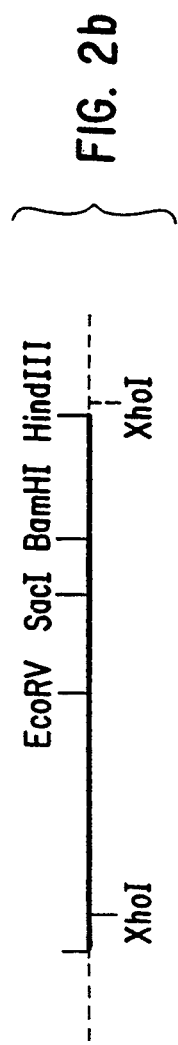
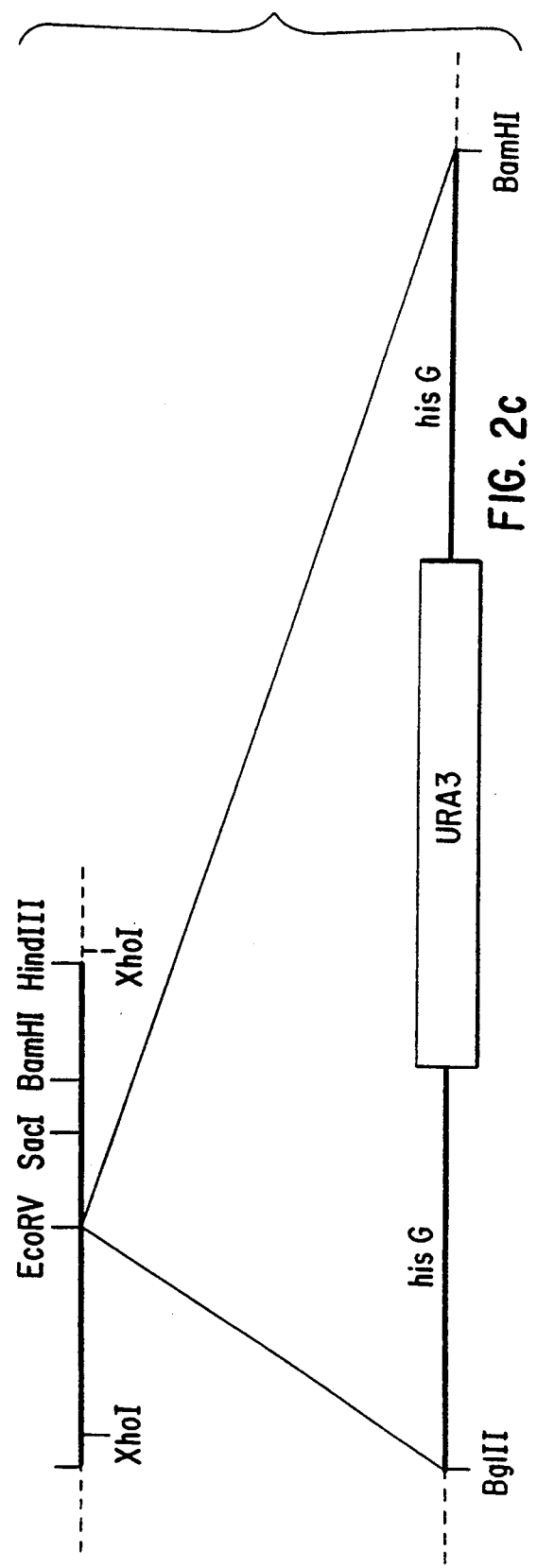

ISOLATION OF STRAINS OF *SACCHAROMYCES CEREVISIAE* HAVING ALTERED ALPHA-ACETYLTRANSFERASE ACTIVITY

CROSS-REFERENCE TO RELATED APPLICATIONS

This application is a continuation of application Ser. No. 07/426,381, filed Oct. 25, 1989, which is a continuation-in-part application of U.S. patent applications Ser. Nos. 07/284,344, filed Dec. 14, 1988, now U.S. Pat. No. 4,966,848 and 07/153,361, filed Feb. 8, 1988, now abandoned the contents of which are fully incorporated herein by reference.

FIELD OF THE INVENTION

The invention is directed to the isolation, purification, and characterization of strains of the yeast, *Saccharomyces cerevisiae* having altered $N^\alpha$-acetyltransferase activity. The invention also includes the altered $N^\alpha$-acetyltransferase enzymes produced by such strains.

BACKGROUND OF THE INVENTION

Amino terminal acylation is an important co-translational modification of proteins in prokaryotic and eukaryotic cells. Although formyl, pyruvoyl, $\alpha$-ketobutyryl, glycosyl, glucuronyl, $\alpha$-aminoacyl, p-glutamyl, myristoyl, and acetyl are well-known $N^\alpha$-acylating groups, it is clear that acetylation is the most common chemical modification of the $\alpha$-$NH_2$ group of eukaryotic proteins (Tsunasawa, S., et al., *Methods Enzymol* 106:165-170 (1984); Driessen, H. P. C., et al., *CRC Crit. Rev. Biochem* 18:281-325 (1985)).

$N^\alpha$-acetylation plays a role in normal eukaryotic translation and processing (Wold, F., *Trends Biochem. Sci.* 9: 256-257, (1984)), and protects against proteolytic degradation (Jornvall, H., *J. Theor. Biol.* 55:1-12 (1975); Rubenstein, P., et al., *J. Biol. Chem.* 254:11142-11147 (1979)). Further, the rate of protein turnover mediated by the ubiquitin-dependent degradation system depends on the presence of a free $\alpha$-$NH_2$ group (Hershko, A., et al., *Proc. Natl. Acad. Sci. U.S.A.* 81:7021-7025 (1984); Bachmair, A., et al., *Science* 234:179-186 (1986)), and this dependence indicates that $N^\alpha$-acetylation may play a crucial role in impeding protein turnover.

After the discovery that an acetyl moiety was the N-terminal blocking group of tobacco mosaic virus coat protein (Narita, K., et al., *Biochim. Biophys. Acta.* 28:184-191 (1958)), and $\alpha$-melanocyte-stimulating peptide (Harris, J. I., et al.. *Biochem J.* 71:451-459 (1959)), a large number of proteins from various organisms have been shown to possess acetylated N-terminal residues (Brown, J. L., et al., *J. Biol. Chem.* 251:1009-1014 (1976); Brown, J. L., et al., *J. Biol. Chem.* 254:1447-1449 (1979)). For example, mouse L-cells and Ehrlich ascites cells have about 80% of their intracellular soluble proteins $N^\alpha$-acetylated (Brown, J. L., et al., *J. Biol. Chem.* 251:1009-1014 (1976); Brown, J. L., et al., *J. Biol. Chem.* 254:1447-1449 (1979)). In lower eukaryotic organisms, about 50% of the soluble proteins are acetylated (Brown, J. L., *Int'l. Conor. Biochem. Abstr.* (International Union of Biochemistry, Canada) Vol. 11:90 (1979)). These data demonstrate that the $N^\alpha$-acetyl group is a very important blocking group. It has been suggested that the biological function of this blocking group may be to protect against premature protein catabolism (Jornvall, H., *J. Theor. Biol* 55:1-12 (1975)) and protein proteolytic degradation (Rubenstein, P. and Deuchler, J., *J. Biol. Chem.* 254:11142 (1979)). However, in mouse L-cells such $N^\alpha$-acetylation does not apparently have this biological function (Brown, J. L., *J. Biol. Chem.* 254:1447 (1979)).

Although a clear general function for $N^\alpha$-acetylation has not been assessed with certainty, some specific effects for a small number of proteins have been observed. Nonacetylated NADP-specific glutamate dehydrogenase in a mutant of *Neurosopra crassa* is heat-unstable, in contrast to the acetylated form (Siddig et al., *J. Mol. Biol.* 137:125 (1980)). A mutant of *Escherichia coli*, in which ribosomal protein S5 is not acetylated, exhibits thermosensitivity (Cumberlidge, A. G. and Isono, K., *J. Mol. Biol.* 131:169 (1979)). $N^\alpha$-acetylation of two of the products from the precursor protein proopiomelanocortin has a profound regulatory effect on the biological activity of these polypeptides; the opioid activity of $\beta$-endorphin is completely suppressed, while the melanotropic effect of $\alpha$-MSH is increased if $N^\alpha$-acetylated (Smyth et al., *Nature* 279:252 (1970); Smyth, D. G. and Zakarian, S., *Nature* 288:613 (1980); and Ramachandran, J. and Li, C. H., *Adv. Enzymol.* 29:391 (1967)). Both acetylated and nonacetylated cytoplasmic actin from cultured Drosophila cells participate in the assembly of microfilaments, the latter, however, with less efficiency (Berger et al., *Biochem. Genet.* 19:321 (1981)). More recently, the rate of protein turnover mediated by the ubiquitin-dependent degradation system was shown to depend on the presence of a free $\alpha$-$NH2$ group at the N-terminus of a protein (Hershko et al., *Proc. Nat'l Acad. Sci. U.S.A.* 81:9021-9025 (1984) and Bachmair et al., *Science* 234:179-186 (1986)), suggesting that $N^\alpha$-acetylation may have a role in impeding protein turnover.

$N^\alpha$-acetylation is mediated by at least one $N^\alpha$-acetyltransferase, which catalyzes the transfer of an acetyl group from acetyl coenzyme A to the $\alpha$-$NH_2$ group of proteins and peptides. $N^\alpha$-acetyltransferases have previously been demonstrated in *E. coli* (Brot, N., et al., *Arch. Biochem. Biophys.* 155:475-477 (1973)), rat liver (Pestana, A., et al., *Biochemistry* 14:1397-1403 (1975); Pestana, A., et al., *Biochemistry* 14:1404-1412 (1975); Yamada, R., et al., 1st *Symposium of the Protein Society* 625:34 (1987)), rat brain (O'Donohue, T. L., *J. Biol. Chem.* 258:2163-2167 (1983)), rat pituitary (Woodford, T. A., et al., *J. Biol. Chem.* 254:4993-4999 (1979); Pease, K. A., et al., *Arch Biochem. Biophys.* 212:177-185 (1981); Gembotski, C. C., *J. Biol. Chem.* 257:10501-10509 (1982); Chappell, M. C., et al., *J. Biol. Chem.* 261:1088-1091 (1986)), bovine pituitary (Gembotski, C. C., *J. Biol. Chem.* 257:10501-10509 (1982)), bovine lens (Granger, M., et al., *Proc. Natl. Acad. Sci. USA* 73:3010-314 (1976)), hen oviduct (Tsunasawa, S., et al., *J. Biochem.* 87:645-650 (1980)), and wheat germ (Kido, H., et al., *Arch Biochem. Biophys.* 208:95-100 (1981)). $N^\alpha$-acetyltransferase enzymes from these sources have, however, never been purified more than 40-fold.

SUMMARY OF THE INVENTION

Acetylation is the most frequently occurring chemical modification of the $\alpha$-$NH_2$ group of eukaryotic proteins and is catalyzed by a $N^\alpha$-acetyltransferase. The purification to homogeneity of an $N^\alpha$-acetyltransferase from *Saccharomyces cerevisiae* and the determination of its substrate specificity (Lee, F-J. S., Lin L-W., and Smith, J. A., *J. Biol. Chem.* 263:14948-14955 (1988)), enabled the isolation of a full-length cDNA encoding this yeast N$^\alpha$-acetyltransferase. This cDNA clone was mutagenized and a null mutation (designated "aaa1") was obtained. The mutation, while not lethal, makes cells grow slowly and heterogeneously. Although aaa1-/AAA1 diploids can form four initially viable spores, the two aaa1 spores within the ascus consistently gave small colonies Furthermore, aaa1/aaa1 diploids are sporulation-defective. aaa1 mutants are sensitive to heat shock and can not enter the stationary phase. The aaa1 mutation also specifically reduces mating functions in "a" mating type cells. These results indicate that N$^\alpha$-acetylation is an important chemical modification of eukaryotic proteins.

The availability of this mutant permits other mutations to be obtained, and has application in gene expression, and protein sequence determination.

In detail, the invention provides, a cell which expresses an altered N$^\alpha$-acetyltransferase. In one embodiment, the invention concerns a yeast cell which expresses an altered N$^\alpha$-acetyltransferase, and particularly a yeast cell having a mutation in the AAA1 gene. Of special interest to the invention are mutations of the AAA1 gene which cause the cell to substantially lack N$^\alpha$-acetyltransferase activity.

The invention also concerns a recombinant molecule containing an altered AAA1 gene.

The invention also concerns a method for producing a peptide or protein lacking an N$^\alpha$-acetylated amino terminus which comprises expressing the peptide or protein in a yeast cell having an AAA1 gene, wherein the gene contains a mutation resulting in the substantial loss of AAA1 gene product activity, and renders the cell unable to catalyze the N$^\alpha$-acetylation of the peptide or protein.

The invention also concerns a method for determining the amino acid sequence of a peptide which comprises:
a. expressing the peptide in a yeast cell having an AAA1 gene, wherein the gene contains a mutation resulting in the substantial loss of AAA1 gene product activity, and renders the cell unable to catalyze N$^\alpha$-acetylation of peptides;
b. recovering the peptide; and
c. determining the amino acid sequence of the peptide.

BRIEF DESCRIPTION OF FIGURES

FIGS. 1A-1D show the sequence of the amino acids of Saccharomyces cerevisiae N$^\alpha$-acetyltransferase AAA1, and its cDNA sequence.

FIG. 2 shows a restriction map of the AAA1 gene. (a) shows the full length AAA1 clone (pBN9) (dark line is cDNA, dashed line is Bluescript); (b) the deletion of the 3' HindIII fragment from pBN9 (pBNH9), and (c) the insertion of the 3.8 kb hisG-URA3-hisG fragment at the EcoRV site of pBNH9 (pBNHU9).

DESCRIPTION OF THE PREFERRED EMBODIMENTS

Figure 3:
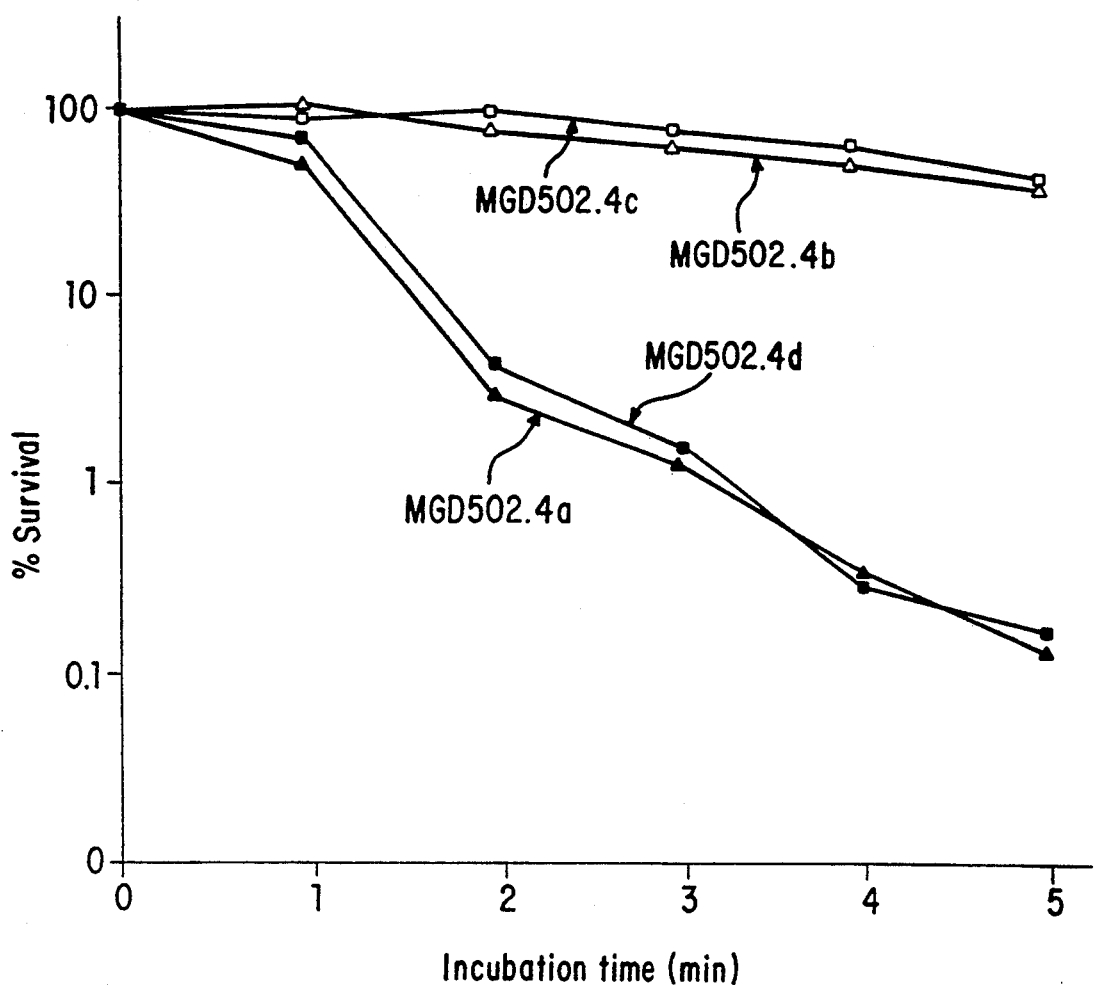
FIG. 3 shows the heat shock sensitivity of the aaa1 strains. Cells were grown to late log phase in YPD medium, diluted in SD medium, and incubated at 54° C. The survival percentage was determined at each indicated time. The genotypes of the strains are shown in Table 2.

The N$^\alpha$-acetyltransferase of Saccharomyces cerevisiae was purified to apparent homogeneity (4600-fold) and characterized as a dimeric protein, whose subunit M$_r$ was 95,000, and which would effectively transfer an acetyl group to various synthetic peptide substrates (including ACTH (1-24), human superoxide dismutase (1-24), and yeast alcohol dehydrogenase (1-24) (Lee, F.-J. S., et al., J. Biol. Chem. 263:14948-14955 (1988), U.S. patent applications Ser. Nos. 07/284,344, and 07/153,361, which references are incorporated herein by reference).

Further, it was demonstrated that this enzyme would not transfer an acetyl group to the ε-amino group of lysyl residues in various peptide substrates and histones. The N$^\alpha$-acetyltransferase enzyme is encoded by a single gene (AAA1, amino-terminal, α-amino, acetyltransferase) which is localized on Saccharomyces cerevisiae chromosome IV.

The purification of the N$^\alpha$-acetyltransferase enzyme permitted the elucidation of its amino acid sequence. This elucidation permitted the identification and cloning of the cDNA sequence which encodes the enzyme in yeast. The cloning of the yeast cDNA permits an investigation the biological function and regulation of N$^\alpha$-acetylation in eukaryotic protein synthesis and degradation.

Specifically, the availability of this cDNA molecule permits the construction of mutant alleles of the Saccharomyces cerevisiae N$^\alpha$-acetyltransferase gene, and the introduction of such altered alleles into yeast and plant cells in order to produce cells which express altered N$^\alpha$-acetyltransferase enzymes. The construction and use of such mutants is described by Lee, F.-J., Lin, L.-W. and Smith, J. A., J. Bacteriol, 171 (11) (November 1989), which reference is incorporated herein by reference.

One aspect of the present invention thus concerns Saccharomyces cerevisiae and plant strains having altered N$^\alpha$-acetyltransferase activity. As used herein, the term "altered" is intended to refer to on between the characteristics of the N$^\alpha$-acetyltransferase activities of the present invention with those of the normal (i.e. non-mutant or "wild-type") enzyme of Saccharomyces cerevisiae. Methods for isolating, purifying and assaying normal Saccharomyces cerevisiae N$^\alpha$-acetyltransferase, and the characteristics of this enzyme (i.e. substrate specificity, specific activity, stability, etc.) are described in U.S. patent applications Nos. 07/284,344, and 07/153,361, which references are incorporated herein by reference.

The altered N$^\alpha$-acetyltransferase activities of the present invention may have for example a lower specific activity (units of activity per unit weight) than that found in normal cells. For example, a "null" mutation (such as the aaa1 mutation discussed below) may be produced to construct a cell whose N$^\alpha$-acetyltransferase lacks substantially all of the N$^\alpha$-acetyltransferase activity associated with the normal protein. When such an allele is introduced into a yeast cell, basic cellular characteristics such as sensitivity to high temperature, entrance of the stationary phase, and mating functions are affected. This result indicates that N$^\alpha$-acetylation is an important chemical modification of eukaryotic proteins and affect several unrelated biological function in eukaryotic cells.

The present invention also includes Saccharomyces cerevisiae strains having an enhanced level of N$^\alpha$-acetyltransferase (i.e. elevated with respect to the normal level). The invention further includes Saccharomyces cerevisiae strains having N$^\alpha$-acetyltransferase activity of altered (i.e. non-normal) specificity, stability, or characteristics.

The present invention also concerns the $N^\alpha$-acetyltransferase enzyme of the present invention, or its variants, which is "substantially pure" or which has been "substantially purified." As used herein, the terms "substantially pure" or "substantially purified" are intended to be equivalent, and to describe an $N^\alpha$-acetyltransferase which is substantially free of a compound normally associated with the enzyme in its natural state, i.e., a protein, carbohydrate, lipid, etc. The term is further meant to describe an $N^\alpha$-acetyltransferase which is homogeneous by one or more of the assays of purity or homogeneity used by those of skill in the art. For example, a substantially pure $N^\alpha$-acetyltransferase will show constant and reproducible characteristics within standard experimental deviations for parameters such as the following: molecular weight, chromatographic techniques, etc. The term "substantially pure", however, is not meant to exclude artificial or synthetic mixtures of the enzyme with other compounds. The term is also not meant to exclude the presence of impurities which do not interfere with the biological activity of the enzyme, and which may be present, for example, due to incomplete purification.

I. Genetic Engineering of $N^\alpha$-Acetyltransferase

A. Sequencing of $N^\alpha$-acetyltransferase

The inventors have completed the molecular cloning and determined the complete cDNA sequence analysis of a eukaryotic $N^\alpha$-acetyltransferase gene (Lee, F-J. S., et al., *J. Biol. Chem.* 263:14948-14955 (1988), U.S. patent applications Ser. Nos. 07/284,344, and 07/153,361). The yeast $N^\alpha$-acetyltransferase protein is encoded by an open reading frame of 2562 bases and consists of 854 amino acids. Its molecular weight calculated from its amino acid composition is 98,575 daltons, and this molecular weight agrees with the subunit $M_r$, estimated to be $95,000 \pm 2,000$. The protein sequence analysis of the native protein revealed it to be N-terminally blocked, it is likely that after the cleavage of N-terminal Met residue that the penultimate seryl residue was acylated (possibly acetylated). Although the enzyme is not known to be a glycoprotein, it contains 6 putative N-glycosylation sites (i.e., Asn-X-Ser (or Thr) sequences) at residues 120–122, 161–163, 643–645, 702–704, 761–763, 792–793. The extended, hydrophilic region between residues 508 and 720 is an unusual structural feature of the molecule, although it is not clear whether this region plays a functional role in the regulation or localization of the enzyme. A comparison of the protein sequences of $N^\alpha$-acetyltransferase to other acetyltransferases does not reveal an appreciable percent similarity between them, although certain short sequences have a greater than 50% similarity. These are likely regions where site-specific mutations should be introduced in early attempts to identify residues involved in catalysis. The sequence of *Saccharomyces cerevisiae* $N^\alpha$-acetyltransferase and its cDNA is shown in FIG. 1.

B. The $N^\alpha$-acetyltransferase Gene

The results of Northern and Southern hybridizations indicate that there is one gene encoding this $N^\alpha$-acetyltransferase. However, it is not clear whether or not yeast contains still other acetyltransferases capable of modifying the $\alpha$-NH$_2$ group of proteins. Further, previous studies on the substrate specificity of the yeast $N^\alpha$-acetyltransferase have clearly demonstrated that this enzyme is not capable of acetylating $\epsilon$-NH$_2$ groups in peptide substrates or in histones, although a histone-specific acetyltransferase has been demonstrated in yeast (Travis, G. H. et al., *J. Biol. Chem.* 259:14406-14412 (1984)).

The AAA1 gene is located on chromosome IV and is positioned immediately adjacent to the 5' flanking sequence of the SIR2 gene. Since SIR2 and three other unlinked SIR gene affect trans repression of the transcription of the HMR and HML genes, which are involved in determining the mating type of haploid yeast, there is no clear-cut relationship between the function of these genes and AAA1.

The cloning of the yeast AAA1 gene allows the molecular details of the role $N^\alpha$-acetylation in the sorting and degradation of eukaryotic proteins to be determined.

C. Formation of Mutant and Altered Alleles of the $N^\alpha$-acetyltransferase Gene Sequence Amino acid sequence variants of the $N^\alpha$-acetyltransferase can be prepared by introducing mutations into the cloned $N^\alpha$-acetyltransferase cDNA sequence. Such variants include, for example deletions from, or insertions or substitutions of, residues within the amino acid sequence shown in FIG. 1. Any combination of deletion, insertion, and substitution may be made. Obviously, unless null mutants are desired, the mutations that will be made in the DNA encoding the variant must not place the sequence out of reading frame and preferably will not create complementary regions that could produce secondary mRNA structure (see EP Patent Application Publication No. 75,444).

At the genetic level, these variants ordinarily are prepared by site-directed mutagenesis of nucleotides in the DNA encoding the $N^\alpha$-acetyltransferase, thereby producing DNA encoding the variant, and thereafter expressing the DNA in recombinant cell culture.

While the site for introducing an amino acid sequence variation may be determined in advance, the mutation per se need not be predetermined. For example, to optimize the performance of a mutation at a given site, random mutagenesis may be conducted at the target codon or region and the expressed $N^\alpha$-acetyltransferase variants screened for the optimal combination of desired activity. Techniques for making substitution mutations at predetermined sites in DNA having a known sequence are well known, for example, site-specific mutagenesis.

Preparation of a $N^\alpha$-acetyltransferase variant in accordance herewith is preferably achieved by site-specific mutagenesis of DNA that encodes an earlier prepared variant or a nonvariant version of the protein. Site-specific mutagenesis allows the production of $N^\alpha$-acetyltransferase variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., DNA 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing, J. et al., *3rd Cleveland Symp. Macromolecules Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (USA) 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells such as JMIOI cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and are typically (though not necessarily) contiguous.

Amino acid sequence insertions include amino and/or carboxylterminal fusions of from one residue to polypeptides of essentially unrestricted length, as well as intrasequence insertions of single or multiple amino acid residues. Intrasequence insertions (i.e., insertions within the complete N$^\alpha$-acetyltransferase encoding sequence) may range generally from about 1 to 10 residues, more preferably 1 to 5. An example of a terminal insertion includes a fusion of a signal sequence, whether heterologous or homologous to the host cell, to the N-terminus of the N$^\alpha$-acetyltransferase to facilitate the secretion of mature N$^\alpha$-acetyltransferase from recombinant hosts.

The third group of variants are those in which at least one amino acid residue in the N$^\alpha$-acetyltransferase, and preferably, only one, has been removed and a different residue inserted in its place. Such substitutions preferably are made in accordance with the following Table 1 when it is desired to modulate finely the characteristics of the N$^\alpha$-acetyltransferase.

TABLE 1

| AMINO ACID SUBSTITUTIONS | |
|---|---|
| Original Residue | Exemplary Substitutions |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native N$^\alpha$-acetyltransferase-encoding nucleic acid, expression of the variant nucleic acid in recombinant cell culture, and, optionally, purification from the cell culture, for example, by immunoaffinity adsorption on a polyclonal anti-N$^\alpha$-acetyltransferase column (to absorb the variant by binding it to at least one remaining immune epitope).

The activity of the cell lysate or purified N$^\alpha$-acetyltransferase variant is then screened in a suitable screening assay for the desired characteristic. For example, a change in the immunological character of the altered N$^\alpha$-acetyltransferase, such as affinity for a given antibody, is measured by a competitive type immunoassay. Modifications of such protein properties as redox or thermal stability, hydrophobicity, susceptibility to proteolytic degradation or the tendency to aggregate with carriers or into multimers are assayed by methods well known to the ordinarily skilled artisan.

In order to identify variant N$^\alpha$-acetyltransferases which lack substantial N$^\alpha$-acetyltransferase activity, clones of the normal (i.e. active) N$^\alpha$-acetyltransferase may be mutagenized, and introduced into a null (aaa1) mutant. Since the majority of transformants will then exhibit $N^\alpha$-acetyltransferase activity, clones lacking $N^\alpha$-acetyltransferase activity can be readily identified.

In an analogous manner, it is possible to identify clones having enhanced or altered $N^\alpha$-acetyltransferase activity. Clones of a null allele (having a 1-10 amino acid substitution or deletion) may be mutagenized and introduced into a cell which is deficient in $N^\alpha$-acetyltransferase activity (such as a null mutant). Clones which, due to the mutagenesis have received a "correcting" or "compensating" mutation will, upon introduction into the cell, express $N^\alpha$-acetyltransferase activity. This activity can be assayed (in the manner described above) and the desired altered variants obtained.

D. The Cloning of the $N^\alpha$-acetyltransferase Gene

Any of a variety of procedures may be used to clone the *Saccharomyces cerevisiae* $N^\alpha$-acetyltransferase gene. One such method entails analyzing a shuttle vector library of cDNA inserts (derived from an $N^\alpha$-acetyltransferase expressing cell) for the presence of an insert which contains the $N^\alpha$-acetyltransferase gene. Such an analysis may be conducted by transfecting cells with the vector and then assaying for $N^\alpha$-acetyltransferase expression. The preferred method for cloning this gene entails determining the amino acid sequence of the $N^\alpha$-acetyltransferase enzyme and using these sequences to design probes capable of hybridizing with $N^\alpha$-acetyltransferase-encoding cDNA. To accomplish this task, one sequences purified $N^\alpha$-acetyltransferase protein or fragments of this protein (obtained, for example, with cyanogen bromide, or with proteases such as papain, chymotrypsin or trypsin (Oike, Y. et al., *J. Biol. Chem.* 257:9751-9758 (1982); Liu, C. et al., *Int. J. Pept. Protein Res.* 21:209-215 (1983)). Preferably, such sequencing is accomplished using automated sequenators. If peptides of more than 10 amino acids are sequenced, the sequence information is generally sufficient to permit one to clone a gene such as the gene for $N^\alpha$-acetyltransferase.

Once the complete molecule, or one or more suitable peptide fragments of the molecule, have been sequenced, the DNA sequences capable of encoding them are examined. Because the genetic code is degenerate, more than one codon may be used to encode a particular amino acid (Watson, J. D., In: *Molecular Biology of the Gene.* 3rd Ed., W. A. Benjamin, Inc., Menlo Park, CA (1977), pp. 356-357). The peptide fragments are analyzed to identify sequences of amino acids which may be encoded by oligonucleotides having the lowest degree of degeneracy. This is preferably accomplished by identifying sequences that contain amino acids which are encoded by only a single codon. Although occasionally such amino acid sequences may be encoded by only a single oligonucleotide, frequently the amino acid sequence can be encoded by any of a set of similar oligonucleotides. Importantly, whereas all of the members of the set contain oligonucleotides which are capable of encoding the peptide fragment and, thus, potentially contain the same nucleotide sequence as the gene which encodes the peptide fragment, only one member of the set contains a nucleotide sequence that is identical to the nucleotide sequence of this gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

In a manner exactly analogous to that described above, one may employ an oligonucleotide (or set of oligonucleotides) which have a nucleotide sequence that is complementary to the oligonucleotide sequence or set of sequences that is capable of encoding the peptide fragment.

A suitable oligonucleotide, or set of oligonucleotides which is capable of encoding a fragment of the $N^\alpha$-acetyltransferase gene (or which is complementary to such an oligonucleotide, or set of oligonucleotides) is identified (using the above-described procedure), synthesized, and hybridized, by means well known in the art, against a DNA or, more preferably, a cDNA preparation derived from yeast cells which are capable of expressing $N^\alpha$-acetyltransferase gene sequences. Techniques of nucleic acid hybridization are disclosed by Maniatis, T. et al., In: *Molecular Cloning, a Laboratory Manual,* Cold Spring Harbor, NY (1982), and by Hames, B. D. and Higgins, S. J., In: *Nucleic Acid Hybridization, a Practical Approach,* IRL Press, Washington, DC (1985), which references are herein incorporated by reference. The source of DNA or cDNA used will preferably have been enriched for $N^\alpha$-acetyltransferase sequences. Such enrichment can most easily be obtained from cDNA obtained by extracting RNA from cells cultured under conditions which are characterized by $N^\alpha$-acetyltransferase expression.

Techniques such as, or similar to, those described above have successfully enabled the cloning of genes for human aldehyde dehydrogenases (Hsu, L. C. et al., *Proc. Natl. Acad. Sci. USA* 82:3771-3775 (1985)), fibronectin (Suzuki, S. et al., *Eur. Mol. Biol. Organ. J.* 4:2519-2524 (1985)), the human estrogen receptor gene (Walter, P. et al., *Proc. Natl. Acad. Sci. USA* 82:7889-7893 (1985)), tissue-type plasminogen activator (Pennica, D. et al., *Nature* 301:214-221 (1983)) and human term placental alkaline phosphatase complementary DNA (Kam, W. et al., *Proc. Natl. Acad. Sci. USA* 82:8715-8719 (1985)).

In a preferred alternative way of cloning the $N^\alpha$-acetyltransferase gene, a library of expression vectors is prepared by cloning DNA or, more preferably cDNA, from a cell capable of expressing $N^\alpha$-acetyltransferase into an expression vector. The library is then screened for members capable of expressing a protein which binds to anti-$N^\alpha$-acetyltransferase antibody, and which has a nucleotide sequence that is capable of encoding polypeptides that have the same amino acid sequence as $N^\alpha$-acetyltransferase or fragments of $N^\alpha$-acetyltransferase.

The cloned $N^\alpha$-acetyltransferase gene, obtained through the methods described above, may be operably linked to an expression vector, and introduced into bacterial, or eukaryotic cells to produce $N^\alpha$-acetyltransferase protein. Techniques for such manipulations are disclosed by Maniatis, T. et al., supra. and are well known in the art.

The DNA sequence coding for $N^\alpha$-acetyltransferase may be derived from a variety of sources. For example, mRNA encoded for $N^\alpha$-acetyltransferase may be isolated from the tissues of any species that produces the enzyme, by using the Northern blot method (Alwine et al., *Method Enzymol.* 68:220-242 (1979)), and labeled oligonucleotide probes. The mRNA may then be converted to cDNA by techniques known to those skilled in the art.

The DNA probe may be labeled with a detectable group. Such detectable group can be any material having a detectable physical or chemical property. Such materials have been well-developed in the field of immunoassays and in general most any label useful in such methods can be applied to the present invention. Particularly useful are enzymatically active groups, such as enzymes (see *Clin. Chem.* 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134,792); fluorescers (see *Clin. Chem.* 25:353 (1979)); chromophores; luminescers such as chemiluminescers and bioluminescers (see *Clin. Chem.* 25:512 (1979)); specifically bindable ligands; proximal interacting pairs; and radioisotopes such as $^3H$, $^{35}S$, $^{32}P$, $^{125}I$ and $^{14}C$. Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled probe can be detected by adding the enzyme for which the label is a cofactor and a substrate for the enzyme. For example, one can use an enzyme which acts upon a substrate to generate a product with a measurable physical property. Examples of the latter include, but are not limited to, beta-galactosidase, alkaline phosphatase and peroxidase.

E. Expression of the $N^\alpha$-acetyltransferase Gene Sequences

DNA or cDNA molecules which encode the $N^\alpha$-acetyltransferase enzyme can be operably linked into an expression vector and introduced into a host cell to enable the expression of the $N^\alpha$-acetyltransferase enzyme by that cell. Two DNA sequences (such as a promoter region sequence and a desired enzyme encoding sequence) are said to be operably linked if the nature of the linkage between the two DNA sequences does not (1) result in the introduction of a frame-shift mutation, (2) interfere with the ability of the promoter region sequence to direct the transcription of the desired enzyme encoding gene sequence, or (3) interfere with the ability of the desired enzyme gene sequence to be transcribed by the promoter region sequence.

A DNA sequence encoding $N^\alpha$-acetyltransferase may be recombined with vector DNA in accordance with conventional techniques, including blunt-ended or stagger-ended termini for ligation, restriction enzyme digestion to provide appropriate termini, filling in of cohesive ends as appropriate, alkaline phosphatase treatment to avoid undesirable joining, and ligation with appropriate ligases.

The present invention encompasses the expression of the desired enzyme in any prokaryotic or eukaryotic cells. In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

The $N^\alpha$-acetyltransferase of the invention may be isolated and purified in accordance with conventional conditions, such as extraction, precipitation, chromatography, affinity chromatography, electrophoresis, or the like.

1. Expression in Prokaryotic Cells

Preferred prokaryotic hosts include bacteria such as *E. coli, Bacillus, Streptomyces, Pseudomonas, Salmonella, Serratia,* etc. The most preferred prokaryotic host is *E. coli.* Bacterial hosts of particular interest include *E. coli* K12 strain 294 (ATCC 31446), *E. coli* X1776 (ATCC 31537), *E. coli* W3110 (F⁻, lambda⁻, prototrophic (ATCC 27325)), and other enterobacterium such as *Salmonella typhimurium* or *Serratia marcescens,* and various *Pseudomonas* species. The prokaryotic host must be compatible with the replicon and control sequences in the expression plasmid.

To express the desired enzyme in a prokaryotic cell (such as, for example, *E. coli, B. subtilis, Pseudomonas, Streptomyces,* etc.), it is necessary to operably link the desired enzyme encoding sequence to a functional prokaryotic promoter. Such promoters may be either constitutive or, more preferably, regulatable (i.e., inducible or derepressible). Examples of constitutive promoters include the int promoter of bacteriophage X, and the bla promoter of the $\beta$-lactamase gene of pBR322, etc. Examples of inducible prokaryotic promoters include the major right and left promoters of bacteriophage $\lambda$ ($P_L$ and $P_R$), the *trp, recA, lacZ, lacI, gal,* and *tac* promoters of *E. coli,* the $\alpha$-amylase (Ulmanen, I., et al., *J. Bacteriol.* 162:176-182 (1985)) and the $\sigma$-28-specific promoters of *B. subtilis* (Gilman, M. Z., et al., *Gene* 32:11-20 (1984)), the promoters of the bacteriophages of *Bacillus* (Gryczan, T. J., In: *The Molecular Biology of the Bacilli.* Academic Press, Inc., NY (1982)), and *Streotomvces* promoters (Ward, J. M., et al., *Mol. Gen. Genet.* 203:468-478 (1986)). Prokaryotic promoters are reviewed by Glick, B. R., (*J. Ind. Microbiol.* 1:277-282 (1987)); Cenatiempo, Y. (*Biochimie* 68:505-516 (1986)); and Gottesman, S. (*Ann. Rev. Genet.* 18:415-442 (1984)).

Proper expression in a prokaryotic cell also requires the presence of a ribosome binding site upstream of the gene-encoding sequence. Such ribosome binding sites are disclosed, for example, by Gold, L., et al. (*Ann. Rev. Microbiol.* 35:365-404 (1981)).

The desired enzyme encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired enzyme may occur through the transient expression of the introduced sequence. Alternatively, permanent expression may occur through the integration of the introduced sequence into the host chromosome.

Preferred prokaryotic vectors include plasmids such as those capable of replication in *E. coli* (such as, for example, pBR322, ColEI, pSCIOI, pACYC 184, πVX. Such plasmids are, for example, disclosed by Maniatis, T., et al. (In: *Molecular Cloning, A Laboratory Manual,* Cold Spring Harbor Press, Cold Spring Harbor, NY (1982)). Bacillus plasmids include pC194, pC221, pT127, etc. Such plasmids are disclosed by Gryczan, T. (In: *The Molecular Biology of the Bacilli,* Academic Press, NY (1982), pp. 307-329). Suitable *Streotomvces* plasmids include pIJ101 (Kendall, K. J., et al., *J. Bacteriol.* 169:4177-4183 (1987)), and streptomyces bacteriophages such as φC31 (Chater, K. F., et al., In: *Sixth International Symposium on Actinomycetales Biology,* Akademiai Kaido, Budapest, Hungary (1986), pp. 45-54). Pseudomonas plasmids are reviewed by John, J. F., et al. (*Rev. Infect. Dis.* 8:693-704 (1986)), and Izaki, K. (*Jpn. J. Bacteriol* 33:729-742 (1978)).

Once the vector or DNA sequence containing the constructs has been prepared for expression, the DNA constructs may be introduced to an appropriate host. Various techniques may be employed, such as protoplast fusion, calcium phosphate precipitation, electroporation or other conventional techniques. After the fusion, the cells are grown in media and screened for appropriate activities. Expression of the sequence results in the production of the substrate-specific aminopeptidase.

2. Expression in Eukaryotic Cells

Preferred eukaryotic hosts include yeast, fungi (especially *Aspergillus*), mammalian cells (such as, for example, human or primate cells) and plant cells either in vivo. or in tissue culture.

The expression of the desired enzyme in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature* (London) 290:304-310 (1981)); the yeast gal4 gene promoter (Johnston, S. A., et al., *Proc. Natl. Acad. Sci.* (USA) 79:6971-6975 (1982); Silver, P. A., et al., *Proc. Natl. Acad. Sci.* (USA) 81:5951-5955 (1984)).

As is widely known, translation of eukaryotic mRNA is initiated at the codon which encodes the first methionine. For this reason, it is preferable to ensure that the linkage between a eukaryotic promoter and a DNA sequence which encodes the desired enzyme (or a functional derivative thereof) does not contain any intervening codons which are capable of encoding a methionine (i.e., AUG). The presence of such codons results either in a formation of a fusion protein (if the AUG codon is in the same reading frame as the desired enzyme encoding DNA sequence) or a frame-shift mutation (if the AUG codon is not in the same reading frame as the desired enzyme encoding sequence).

a. Expression in Yeast

Yeast are the preferred hosts of the present invention. The use of yeast provides substantial advantages in that yeast can also carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

Any of a series of yeast gene expression systems can be utilized. Examples of such expression vectors include the yeast 2-micron circle, the expression plasmids YEP13, YCP and YRP, etc., or their derivatives. Such plasmids are well known in the art (Botstein, D., et al., *Miami Wntr. Symp.* 19:265-274 (1982); Broach, J. R., In: *The Molecular Biology of the Yeast Saccharomyces: Life Cycle and Inheritance.* Cold Spring Harbor Laboratory, Cold Spring Harbor, NY, p. 445-470 (1981); Broach, J. R., *Cell* 28:203-204 (1982)). YEP13 is the preferred vector of the present invention.

b. Expression in Mammalian Cells

Mammalian cells provide post-translational modifications to protein molecules including correct folding or glycosylation at correct sites. Mammalian cells which may be useful as hosts include cells of fibroblast origin such as VERO or CHO-K1, and their derivatives. For a mammalian host, several possible vector systems are available for the expression of the desired enzyme. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others.

c. Expression in Plant Cells

The $N^\alpha$-acetyltransferase can be introduced into a plant by genetic engineering techniques to enhance the rate of acetylation. It is known that certain herbicides are inactivated by acetylation. Therefore, it is possible to produce a plant that is more herbicide-tolerant. In thus another embodiment of this invention, the $N^\alpha$-acetyltransferase gene is used to transform a plant to enhance the herbicidal tolerance of the plant.

The coding region for a $N^\alpha$-acetyltransferase gene that may be used in this invention may be homologous or heterologous to the plant cell or plant being transformed. It is necessary, however, that the genetic sequence coding for $N^\alpha$-acetyltransferase be expressed, and produced, as a functional protein or polypeptide in the resulting plant cell. Thus, the invention comprises plants containing either homologous $N^\alpha$-acetyltransferase genes or heterologous $N^\alpha$-acetyltransferase genes that express the enzyme.

In one embodiment of this invention, the $N^\alpha$-acetyltransferase comprises a plant $N^\alpha$-acetyltransferase that is homologous to the plant to be transformed. In another embodiment of this invention, the $N^\alpha$-acetyltransferase comprises an enzyme that is heterologous to the plant to be transformed. Moreover, DNA from both genomic DNA and cDNA encoding a $N^\alpha$-acetyltransferase gene may be used in this invention. Further, a $N^\alpha$-acetyltransferase gene may be constructed partially of a cDNA clone and partially of a genomic clone. In addition, the DNA coding for the $N^\alpha$-acetyltransferase gene may comprise portions from various species.

There are a variety of embodiments encompassed in the broad concept of the invention. In one of its embodiments, this invention comprises chimeric genetic sequences:

(a) a first genetic sequence coding for a $N^\alpha$-acetyltransferase that upon expression of the gene in a given plant cell is functional for $N^\alpha$-acetyltransferase;

(b) one or more additional genetic sequences operably linked on either side of the $N^\alpha$-acetyltransferase coding region. These additional genetic sequences contain sequences for promoter(s) or terminator(s). The plant regulatory sequences may be heterologous or homologous to the host cell.

In a preferred embodiment, the promoter of the $N^\alpha$-acetyltransferase gene is used to express the chimeric genetic sequence. Other promoters that may be used in the genetic sequence include nos, ocs, and CaMV promoters. An efficient plant promoter that may be used is an overproducing plant promoter. This promoter in operable linkage with the genetic sequence for $N^\alpha$-acetyltransferase should be capable of promoting expression of said $N^\alpha$-acetyltransferase such that the transformed plant has increased tolerance to a herbicide. Overproducing plant promoters that may be used in this invention include the promoter of the small subunit (ss) of the ribulose-1,5-biphosphate carboxylase from soybean (Berry-Lowe et al., *J. Molecular and Aoo. Gen.*. 1:483–498 (1982)), and the promoter of the chlorophyll a/b binding protein. These two promoters are known to be light induced in eukaryotic plant cells (see, for example, *Genetic Engineering of Plants, an Agricultural Perspective*, A. Cashmore, Plenum, New York 1983, pages 29–38; Corruzi, G. et al., *J. of Biol. Chem.*. 258: 1399 (1983); and Dunsmuir, P. et al., *J. of Mol. and Applied Genet.*, 2: 285 (1983)).

Further, in another preferred embodiment, the expression of the chimeric genetic sequence comprising the $N^\alpha$-acetyltransferase gene is operably linked in correct reading frame with a plant promoter and with a gene secretion signal sequence.

The chimeric genetic sequence comprising a $N^\alpha$-acetyltransferase gene operably linked to a plant promoter, and in the preferred embodiment with the secretion signal sequences, can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells, typically resistance to antibiotics. The transforming vectors can be selected by these phenotypic markers after transformation in a host cell.

Host cells that may be used in this invention include prokaryotes, including bacterial hosts such as *E. coli. S. typhimurium*, and *Serratia marcescens*. Eukaryotic hosts such as yeast or filamentous fungi may also be used in this invention.

The cloning vector and host cell transformed with the vector are used in this invention typically to increase the copy number of the vector. With an increased copy number, the vectors containing the $N^\alpha$-acetyltransferase gene can be isolated and, for example, used to introduce the chimeric genetic sequences into the plant cells. The genetic material contained in the vector can be microinjected directly into plant cells by use of micropipettes to mechanically transfer the recombinant DNA. The genetic material may also be transferred into the plant cell by using polyethylene glycol which forms a precipitation complex with the genetic material that is taken up by the cell.

In an alternative embodiment of this invention, the $N^\alpha$-acetyltransferase gene may be introduced into the plant cells by electroporation. (Fromm et al., "Expression of Genes Transferred into Monocot and Dicot Plant Cells by Electroporation," *Proc. Nat'l. Acad. Sci. U.S.A.* 82:5824 (1985)). In this technique, plant protoplasts are electroporated in the presence of plasmids containing the $N^\alpha$-acetyltransferase genetic construct. Electrical impulses of high field strength reversibly permeabilize biomembranes allowing the introduction of the plasmids. Electroporated plant protoplasts reform the cell wall, divide, and form plant callus. Selection of the transformed plant cells with the expressed $N^\alpha$-acetyltransferase can be accomplished using the phenotypic markers as described above.

Another method of introducing the $N^\alpha$-acetyltransferase gene into plant cells is to infect a plant cell with *Agrobacterium tumefaciens* transformed with the $N^\alpha$-acetyltransferase gene. Under appropriate conditions known in the art, the transformed plant cells are grown to form shoots, roots, and develop further into plants. The $N^\alpha$-acetyltransferase genetic sequences can be introduced into appropriate plant cells, for example, by means of the Ti plasmid of *Agrobacterium tumefaciens*. The Ti plasmid is transmitted to plant cells on infection by *Agrobacterium tumefaciens* and is stably integrated into the plant genome. (Horsch et al., "Inheritance of Functional Foreign Genes in Plants," *Science* 233:496–498 (1984); Fraley et al., *Proc. Nat'l Acad. Sci. U.S.A.* 80:4803 (1983)).

Ti plasmids contain two regions essential for the production of transformed cells. One of these, named transfer DNA (T DNA), induces tumor formation. The other, termed virulent region, is essential for the formation but not maintenance of tumors. The transfer DNA region, which transfers to the plant genome, can be increased in size by the insertion of the enzyme's genetic sequence without its transferring ability being affected. By removing the tumor-causing genes so that they no longer interfere, the modified Ti plasmid can then be used as a vector for the transfer of the gene constructs of the invention into an appropriate plant cell.

All plant cells which can be transformed by *Agrobacterium* and whole plants regenerated from the transformed cells can also be transformed according to the invention so to produce transformed whole plants which contain the transferred $N^\alpha$-acetyltransferase gene.

There are presently two different ways to transform plant cells with *Agrobacterium:*
(1) co-cultivation of *Agrobacterium* with cultured isolated protoplasts, or
(2) transforming cells or tissues with *Agrobacterium*.

Method (1) requires an established culture system that allows culturing protoplasts and plant regeneration from cultured protoplasts.

Method (2) requires (a) that the plant cells or tissues can be transformed by *Agrobacterium* and (b) that the transformed cells or tissues can be induced to regenerate into whole plants. In the binary system, to have infection, two plasmids are needed: a T-DNA containing plasmid and a vir plasmid.

After transformation of the plant cell or plant, those plant cells or plants transformed by the Ti plasmid so that the enzyme is expressed, can be selected by an appropriate phenotypic marker. These phenotypical markers include, but are not limited to, antibiotic resistance. Other phenotypic markers are known in the art and may be used in this invention.

All plants from which protoplasts can be isolated and cultured to give whole regenerated plants can be transformed by the present invention so that whole plants are recovered which contain the transferred $N^\alpha$-acetyltransferase gene. Some suitable plants include, for example, species from the genera Fragaria, Lotus, Medicaqo, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hemerocallis, Nemesia, Pelaroonium, Panicum, Pennisetum, Ranunculus, Senecio, Saloiglossis, Cucumis, Browallia, Glycine, Lolium, Zea, Triticum, Sorghum, and Datura.

There is an increasing body of evidence that practically all plants can be regenerated from cultured cells or tissues, including but not limited to all major cereal crop species, sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Monocotyledonous plants, and in particular, cereals and grasses, are not natural hosts to Agrobacterium. Attempts to transform them using Agrobacterium have been unsuccessful until recently. (Hooykas-Van Slogteren et al., *Nature* 311:763–764 (1984).) There is growing evidence now that certain monocots can be transformed by Aqrobacterium. Using novel experimental approaches that have now become available, cereal and grass species may be transformable.

Additional plant genera that may be transformed by Agrobacterium include Ipomoea, Passiflora, Cyclamen, Malus, Prunus, Rosa, Rubus, Populus, Santalum, Allium, Lilium, Narcissus, Ananas, Arachis, Phaseolus, and Pisum.

Plant regeneration from cultural protoplasts is described in Evans et al., "Protoplast Isolation and Culture," in *Handbook of Plant Cell Culture* 1:124–176 (MacMillan Publishing Co., New York, 1983); M. R. Davey, "Recent Developments in the Culture and Regeneration of Plant Protoplasts," ProtoDlasts. 1983 - Lecture Proceedings, pp. 19–29 (Birkhauser, Basel, 1983); P. J. Dale, "Protoplast Culture and Plant Regeneration of Cereals and Other Recalcitrant Crops," in Protoplasts 1983 - Lecture Proceedings, pp. 31–41 (Birkhauser, Basel, 1983); and H. Binding, "Regeneration of Plants," in *Plant Protoplasts.* pp. 21–37 (CRC Press, Boca Raton, 1985).

Regeneration varies from species to species of plants, but generally a suspension of transformed protoplasts containing multiple copies of the $N^\alpha$-acetyltransferase gene is first provided. Embryo formation can then be induced from the protoplast suspensions, to the stage of ripening and germination as natural embryos. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed to produce an inbred plant. The inbred plant produces seed containing the gene for the increased $N^\alpha$-acetyltransferase. These seeds can be grown to produce plants that have enhanced rate of acetylation.

The inbreds according to this invention can be used to develop herbicide tolerant hybrids. In this method, a herbicide tolerant inbred line is crossed with another inbred line to produce the hybrid.

Parts obtained from the regenerated plant, such as flowers, seeds, leaves, branches, fruit, and the like are covered by the invention provided that these parts comprise the herbicidal tolerant cells. Progeny and variants, and mutants of the regenerated plants are also included within the scope of this invention.

In diploid plants, typically one parent may be transformed by the $N^\alpha$-acetyltransferase genetic sequence and the other parent is the wild type. After crossing the parents, the first generation hybrids (F1) will show a distribution of $\frac{1}{2}$ $N^\alpha$-acetyltransferase/wild type:$\frac{1}{2}N^\alpha$-acetyltransferase/wild type. These first generation hybrids (F1) are selfed to produce second generation hybrids (F2). The genetic distribution of the F2 hybrids are $\frac{1}{4}$ $N^\alpha$-acetyltransferase/$N^\alpha$-acetyltransferase $\frac{1}{2}$ $N^\alpha$-acetyltransferase/wild type $\frac{1}{4}$ wild type/wild type. The F2 hybrids with the genetic makeup of $N^\alpha$-acetyltransferase/$N^\alpha$-acetyltransferase are chosen as the herbicidal tolerant plants.

As used herein, variant describes phenotypic changes that are stable and heritable, including heritable variation that is sexually transmitted to progeny of plants, provided that the variant still comprises a herbicidal tolerant plant through enhanced rate of acetylation. Also, as used herein, mutant describes variation as a result of environmental conditions, such as radiation, or as a result of genetic variation in which a trait is transmitted meiotically according to well-established laws of inheritance. The mutant plant, however, must still exhibit a herbicidal tolerance through enhanced rate of acetylation as according to the invention.

II. Uses of the strains of the present invention and their $N^\alpha$-Acetyltransferases As discussed above, the present invention provides a means for producing altered $N^\alpha$-acetyltransferase enzymes, and for introducing gene sequences which encode these enzymes into diverse hosts.

Cells which lack $N^\alpha$-acetyltransferase activity (i.e. which express an altered $N^\alpha$-acetyltransferase substantially lacking $N^\alpha$-acetyltransferase activity) are highly desirable in facilitating the determination of the amino acid sequence of proteins. As discussed above, the presence of $N^\alpha$-acetyl groups on the amino acids of proteins greatly encumbers efforts to determine the amino acid sequence of such molecules. Since a cell which lacks $N^\alpha$-acetyltransferase activity would not catalyze the transfer of acetyl groups to the amino terminus of proteins, a protein produced in such a cell could be readily sequenced. Thus, for example, a cell carrying a null mutation in its $N^\alpha$-acetyltransferase gene (such as the aaa1-1 mutation of *Saccharomyces cerevisiae*) could be used to produce endogenous yeast proteins lacking $N^\alpha$-acetylation. Such cells, for example, may be used to express a recombinant protein or peptide lacking an acetyl group at the protein's (or peptide's) α-amino group. Such proteins could be easily sequenced using known methods.

In a similar manner, such a null mutant cell could be used as a host for the production of heterologous proteins (i.e. proteins not naturally or normally produced by such a cell) in order to facilitate the elucidation of the amino acid sequence of such proteins.

The ability to produce mutant cells whose $N^\alpha$-acetyltransferase is more active, or produced at higher levels, than normal $N^\alpha$-acetyltransferase, is desirable when one wishes to produce proteins having increased $N^\alpha$-acetylation. As discussed above, such proteins are desirable in being more stable than non-acetylated proteins.

The ability to alter the $N^\alpha$-acetyltransferase activity to conform to a desired activity (such as increased or decreased substrate specificity, thermal stability, etc.) is useful in permitting the development of host cells capable of producing proteins having altered $N^\alpha$-acetylation characteristics.

The altered $N^\alpha$-acetyltransferase enzymes can be purified and used in vitro in the same manner as described above for the mutant host cells.

Having now generally described this invention, the same will be better understood by reference to specific examples, which are included herein for purposes of illustration only, and are not intended to be limiting unless otherwise specified.

EXAMPLE 1

Growth of Yeast Cells

Yeast culture media were prepared, as described by Sherman et al. (Sherman, F., et al., *Methods in Yeast Genetics*, Cold Spring Harbor Laboratory, Cold Spring Harbor, NY (1986)): YPD contained 1% Bacto-yeast extract, 2% Bacto-peptone, and 2% glucose; YPG contained 1% Bacto-yeast extract, 2% Bacto-peptone, and 3% glycerol; SD contained 0.7% Difco yeast nitrogen base without amino acids and 2% glucose; and nutrients essential for auxotrophic strains were supplied at specified concentrations (Sherman, F., et al., *Methods in Yeast Genetics*. Cold Spring Harbor Laboratory, Cold Spring Harbor, NY (1986)).

EXAMPLE 2

Isolation, Purification and Assay of $N^\alpha$-Acetyltransferase

A preferred method for purifying the normal and altered $N^\alpha$-acetyltransferases of the present invention is that of Lee, F.-J. S., et al. (*J. Biol. Chem.* 263:14948–14955 (1988), which reference is incorporated by reference herein in its entirety). In brief, the methods isolates $N^\alpha$-acetyltransferase by treating yeast cells with lyticase and then homogenizing the resulting spheroplasts in a hypotonic buffer. Yeast $N^\alpha$-acetyltransferase is released from the cell lysate by gentle shaking. The $N^\alpha$-acetyltransferase may be concentrated, as by ultrafiltration with PM-30 membrane, and dialyzed overnight using, for example, HDG buffer (20 mM HEPES-K+, pH 7.4, 0.5 mM DTT, 10% (v/v) glycerol and 0.02% NaN$_3$) containing 0.2 M KCl. The half-life of yeast $N^\alpha$-acetyltransferase preparations may be stabilized by the addition of 10% glycerol.

The $N^\alpha$-acetyltransferase preparation may optionally be further purified by the removal of residual cell biomaterials in the supernatant. Ion exchange can be used for this procedure. DEAE-Sepharose chromatography with constant salt (0.2 M KCl) elute is a preferred procedure.

If desired, $N^\alpha$-acetyltransferase may be further purified by pooling and concentrating peak fractions from the ion exchange chromatography, dialyzing against suitable buffer (such as HDG buffer containing 0.05 M KCl), and loading onto an ion exchange resin (for example, DEAE-Sepharose) column with a continuous salt gradient (for example, 0.05 to 0.5 M KCl) elute. The acetyltransferase pool from this column may be concentrated, dialyzed, and analyzed for acetyltransferase activity.

Peak fractions from the ion exchange column may be further purified through the use of an adsorption column using hydroxylapatite. As is known in the art, a hydroxylapatite column will selectively adsorb proteins onto calcium ions in the calcium hydroxyphosphate packing. The hydroxylapatite column is preferably eluted with a linear salt gradient and active fractions can be identified and pooled.

If desired, peak fractions from the hydroxylapatite column may be pooled, concentrated, dialyzed against suitable buffer (such as HDG buffer containing 0.05 M KCl), and loaded onto an ion exhange column, preferably DE52-cellulose, with a continuous salt gradient.

Peak fractions from DE52-cellulose column may be further purified, if desired, by pooling the active fractions, concentrating the $N^\alpha$-acetyltransferase activity, dialyzing against suitable buffer (such as HDG buffer containing 0.05 M KCl), and application onto an affinity column, such as Affi-Blue gel, with a continuous salt gradient (such as 0.05 to 1.0 M KCl) elute. A single activity peak is generated which centered at 0.6 M KCl.

Using this series of chromatography steps, yeast acetyltransferase may be purified approximately 4600-fold over the cell extract with a 27% yield. $N^\alpha$-acetyltransferase activity may be measured as follows: Crude yeast lysates were prepared, and $N^\alpha$-acetyltransferase activity was determined as previously described (Lee, F.-J. S., et al., *J. Biol. Chem.* 263:14948–14955 (1989)). Aliquots of the lysate were added to 1.5 ml Eppendorf tubes containing a reaction mixture of 50 mM HEPES, pH 7.4, 150 mM KCl, 1 mM DTT, 25 μM[³H]acetyl coenzyme A (0.5 μCi) and 50 μM ACTH (1-24) with an adjusted final volume of 100 μl. The assay mixture was incubated at 30 C for 30 min. The reaction was stopped by adding 0.5 M acetic acid and chilled in an ice bath. The reaction samples were filtered through SP membrane discs (Cuno), and then washed with 0.5 M acetic acid on a Millipore 1225 sampling manifold. The partially dried membranes were placed in scintillation cocktail and counted with a Beckman LS 3801 scintillation counter. The radioactivity in the control represented acetylation of endogenous compounds is subtracted from each sample determination. One unit of activity is defined as 1 pmol of acetyl residues incorporated into ACTH (1-24) under standard assay conditions.

As used herein, the term "substantially pure" or "substantially purified" is meant to describe $N^\alpha$-acetyltransferase which is substantially free of any compound normally associated with the enzyme in its natural state, i.e., free of protein and carbohydrate components. The term is further meant to describe $N^\alpha$-acetyltransferase which is homogeneous by one or more purity or homogeneity characteristics used by those of skill in the art. For example, a substantially pure $N^\alpha$-acetyltransferase will show constant and reproducible characteristics within standard experimental deviations for parameters such as the following: molecular weight, chromatographic techniques, and such other parameters. The term, however, is not meant to exclude artificial or synthetic mixtures of the enzymes with other compounds. The term is also not meant to exclude the presence of minor impurities which do not interfere with the biological activity of the enzyme, and which may be present, for example, due to incomplete purification.

EXAMPLE 3

Comparative Specificity of $N^\alpha$-Acetyltransferases

The aaa1 mutant was found to possess a second, hitherto unsuspected $N^\alpha$-acetyltransferase. This second $N^\alpha$-acetyltransferase is a methionine $N^\alpha$-acetyltransferase activity, and is designated as "M-$N^\alpha$-AT." This second $N^\alpha$-acetyltransferase is the subject of U.S. patent application of John A. Smith and Fang-Jen S. Lee, filed Oct. 25, 1989, entitled "IDENTIFICATION OF METHIONINE $N^\alpha$-ACETYLTRANSFERASE," which reference is incorporated herein by reference. In order to compare the relative specificity and activity of the AAA1 $N^\alpha$-acetyltransferase ("$N^\alpha$-AT") of the present invention with the methionine $N^\alpha$-acetyltransferase activity (M-$N^\alpha$-AT) of U.S. patent application of John A. Smith and Fang-Jen S. Lee, filed Oct. 25, 1989, entitled "IDENTIFICATION OF METHIONINE $N^\alpha$-ACETYLTRANSFERASE," synthetic peptides were prepared. These peptides were assessed for their ability to serve as substrates for the two enzymes. The results of this experiment are shown in Tables 2 and 3. In Table 2, the effect of the amino terminal amino acid on activity is investigated; in Table 3, the effect of the penultimate amino terminal amino acid on activity is investigated.

TABLE 2

RELATIVE ACTIVITY OF YEAST ACETYLTRANSFERASES $N^\alpha$-AT AND M-$N^\alpha$-AT FOR THE $N^\alpha$-ACETYLATION OF SYNTHETIC PEPTIDES: INFLUENCE OF THE AMINO TERMINAL RESIDUE

| Substrate | Activity (%) (mean activity ± S.D.) | |
|---|---|---|
| | $N^\alpha$-AT | M-$N^\alpha$-AT |
| ACTH (Human) S-Y-S-M-E-H-F-R-W-G-K-P-V-G-K-K-R-R-P-V-K-V-Y-P | 100 ± 5 | 0 |
| ALCOHOL DEHYDROGENASE I (1-24) (Yeast) S-I-P-E-T-Q-K-G-V-I-F-Y-E-S-H-G-K-L-E-Y-K-D-I-P | 102 ± 5 | 0 |
| [A¹] ALCOHOL DEHYDROGENASE I (1-24) (Yeast) A-I-P-E-T-Q-K-G-V-I-F-Y-E-S-H-G-K-L-E-Y-K-D-I-P | 0 | 0 |
| [R¹] ALCOHOL DEHYDROGENASE I (1-24) (Yeast) R-I-P-E-T-Q-K-G-V-I-F-Y-E-S-H-G-K-L-E-Y-K-D-I-P | 0 | 0 |
| [N¹] ALCOHOL DEHYDROGENASE I (1-24) (Yeast) N-I-P-E-T-Q-K-G-V-I-F-Y-E-S-H-G-K-L-E-Y-K-D-I-P | 0 | 0 |
| [D¹] ALCOHOL DEHYDROGENASE I (1-24) (Yeast) D-I-P-E-T-Q-K-G-V-I-F-Y-E-S-H-G-K-L-E-Y-K-D-I-P | 0 | 0 |
| [C¹] ALCOHOL DEHYDROGENASE I (1-24) (Yeast) C-I-P-E-T-Q-K-G-V-I-F-Y-E-S-H-G-K-L-E-Y-K-D-I-P | 0 | 0 |
| [Q¹] ALCOHOL DEHYDROGENASE I (1-24) (Yeast) Q-I-P-E-T-Q-K-G-V-I-F-Y-E-S-H-G-K-L-E-Y-K-D-I-P | 0 | 0 |
| [E¹] ALCOHOL DEHYDROGENASE I (1-24) (Yeast) E-I-P-E-T-Q-K-G-V-I-F-Y-E-S-H-G-K-L-E-Y-K-D-I-P | 0 | 0 |
| [G¹] ALCOHOL DEHYDROGENASE I (1-24) (Yeast) G-I-P-E-T-Q-K-G-V-I-F-Y-E-S-H-G-K-L-E-Y-K-D-I-P | 23 ± 3 | 0 |
| [I¹] ALCOHOL DEHYDROGENASE I (1-24) (Yeast) I-I-P-E-T-Q-K-G-V-I-F-Y-E-S-H-G-K-L-E-Y-K-D-I-P | 0 | 0 |
| [L¹] ALCOHOL DEHYDROGENASE I (1-24) (Yeast) L-I-P-E-T-Q-K-G-V-I-F-Y-E-S-H-G-K-L-E-Y-K-D-I-P | 0 | 0 |
| [H¹] ALCOHOL DEHYDROGENASE I (1-24) (Yeast) H-I-P-E-T-Q-K-G-V-I-F-Y-E-S-H-G-K-L-E-Y-K-D-I-P | 19 ± 2 | 0 |
| [K¹] ALCOHOL DEHYDROGENASE I (1-24) (Yeast) K-I-P-E-T-Q-K-G-V-I-F-Y-E-S-H-G-K-L-E-Y-K-D-I-P | 0 | 0 |
| [M¹] ALCOHOL DEHYDROGENASE I (1-24) (Yeast) M-I-P-E-T-Q-K-G-V-I-F-Y-E-S-H-G-K-L-E-Y-K-D-I-P | 15 ± 2 | 0 |
| [F¹] ALCOHOL DEHYDROGENASE I (1-24) (Yeast) F-I-P-E-T-Q-K-G-V-I-F-Y-E-S-H-G-K-L-E-Y-K-D-I-P | 9 ± 2 | 0 |
| [P¹] ALCOHOL DEHYDROGENASE I (1-24) (Yeast) P-I-P-E-T-Q-K-G-V-I-F-Y-E-S-H-G-K-L-E-Y-K-D-I-P | 70 ± 4 | 0 |
| [T¹] ALCOHOL DEHYDROGENASE I (1-24) (Yeast) T-I-P-E-T-Q-K-G-V-I-F-Y-E-S-H-G-K-L-E-Y-K-D-I-P | 103 ± 5 | 0 |

TABLE 2-continued

RELATIVE ACTIVITY OF YEAST ACETYLTRANSFERASES $N^\alpha$-AT AND M-$N^\alpha$-AT
FOR THE $N^\alpha$-ACETYLATION OF SYNTHETIC PEPTIDES:
INFLUENCE OF THE AMINO TERMINAL RESIDUE

| Substrate | Activity (%) (mean activity ± S.D.) | |
|---|---|---|
|  | $N^\alpha$-AT | M-$N^\alpha$-AT |
| [W¹] ALCOHOL DEHYDROGENASE I (1-24) (Yeast) W-I-P-E-T-Q-K-G-V-I-F-Y-E-S-H-G-K-L-E-Y-K-D-I-P | 0 | 0 |
| [Y¹] ALCOHOL DEHYDROGENASE I (1-24) (Yeast) Y-I-P-E-T-Q-K-G-V-I-F-Y-E-S-H-G-K-L-E-Y-K-D-I-P | 20 ± 2 | 0 |
| [V¹] ALCOHOL DEHYDROGENASE I (1-24) (Yeast) V-I-P-E-T-Q-K-G-V-I-F-Y-E-S-H-G-K-L-E-Y-K-D-I-P | 69 ± 4 | 0 |

TABLE 3

RELATIVE ACTIVITY OF YEAST ACETYLTRANSFERASES $N^\alpha$-AT AND M-$N^\alpha$-AT
FOR THE $N^\alpha$-ACETYLATION OF SYNTHETIC PEPTIDES:
INFLUENCE OF THE PENULTIMATE AMINO TERMINAL RESIDUE

| Substrate | Activity (%) (mean activity ± S.D.) | |
|---|---|---|
|  | $N^\alpha$-AT | M-$N^\alpha$-AT |
| ACTH (Human) S-Y-S-M-E-H-F-R-W-G-K-P-V-G-K-K-R-R-P-V-K-V-Y-P | 100 ± 5 | 0 |
| ALCOHOL DEHYDROGENASE I (1-24) (Yeast) S-I-P-E-T-Q-K-G-V-I-F-Y-E-S-H-G-K-L-E-Y-K-D-I-P | 102 ± 5 | 0 |
| [A²] ALCOHOL DEHYDROGENASE I (1-24) (Yeast) S-A-P-E-T-Q-K-G-V-I-F-Y-E-S-H-G-K-L-E-Y-K-D-I-P | 168 ± 8 | 0 |
| [R²] ALCOHOL DEHYDROGENASE I (1-24) (Yeast) S-R-P-E-T-Q-K-G-V-I-F-Y-E-S-H-G-K-L-E-Y-K-D-I-P | 102 ± 5 | 0 |
| [N²] ALCOHOL DEHYDROGENASE I (1-24) (Yeast) S-N-P-E-T-Q-K-G-V-I-F-Y-E-S-H-G-K-L-E-Y-K-D-I-P | 116 ± 5 | 0 |
| [D²] ALCOHOL DEHYDROGENASE I (1-24) (Yeast) S-D-P-E-T-Q-K-G-V-I-F-Y-E-S-H-G-K-L-E-Y-K-D-I-P | 171 ± 9 | 0 |
| [C²] ALCOHOL DEHYDROGENASE I (1-24) (Yeast) S-C-P-E-T-Q-K-G-V-I-F-Y-E-S-H-G-K-L-E-Y-K-D-I-P | 136 ± 7 | 0 |
| [Q²] ALCOHOL DEHYDROGENASE I (1-24) (Yeast) S-Q-P-E-T-Q-K-G-V-I-F-Y-E-S-H-G-K-L-E-Y-K-D-I-P | 134 ± 7 | 0 |
| [E²] ALCOHOL DEHYDROGENASE I (1-24) (Yeast) S-E-P-E-T-Q-K-G-V-I-F-Y-E-S-H-G-K-L-E-Y-K-D-I-P | 121 ± 6 | 0 |
| [G²] ALCOHOL DEHYDROGENASE I (1-24) (Yeast) S-G-P-E-T-Q-K-G-V-I-F-Y-E-S-H-G-K-L-E-Y-K-D-I-P | 84 ± 5 | 0 |
| [L²] ALCOHOL DEHYDROGENASE I (1-24) (Yeast) S-L-P-E-T-Q-K-G-V-I-F-Y-E-S-H-G-K-L-E-Y-K-D-I-P | 126 ± 5 | 0 |
| [H²] ALCOHOL DEHYDROGENASE I (1-24) (Yeast) S-H-P-E-T-Q-K-G-V-I-F-Y-E-S-H-G-K-L-E-Y-K-D-I-P | 125 ± 6 | 0 |
| [K²] ALCOHOL DEHYDROGENASE I (1-24) (Yeast) S-K-P-E-T-Q-K-G-V-I-F-Y-E-S-H-G-K-L-E-Y-K-D-I-P | 151 ± 6 | 0 |
| [M²] ALCOHOL DEHYDROGENASE I (1-24) (Yeast) S-M-P-E-T-Q-K-G-V-I-F-Y-E-S-H-G-K-L-E-Y-K-D-I-P | 140 ± 7 | 0 |
| [F²] ALCOHOL DEHYDROGENASE I (1-24) (Yeast) S-F-P-E-T-Q-K-G-V-I-F-Y-E-S-H-G-K-L-E-Y-K-D-I-P | 118 ± 6 | 0 |
| [P²] ALCOHOL DEHYDROGENASE I (1-24) (Yeast) S-P-P-E-T-Q-K-G-V-I-F-Y-E-S-H-G-K-L-E-Y-K-D-I-P | 0 | 0 |
| [S²] ALCOHOL DEHYDROGENASE I (1-24) (Yeast) S-S-P-E-T-Q-K-G-V-I-F-Y-E-S-H-G-K-L-E-Y-K-D-I-P | 140 ± 6 | 0 |
| [T²] ALCOHOL DEHYDROGENASE I (1-24) (Yeast) S-T-P-E-T-Q-K-G-V-I-F-Y-E-S-H-G-K-L-E-Y-K-D-I-P | 144 ± 8 | 0 |
| [W²] ALCOHOL DEHYDROGENASE I (1-24) (Yeast) S-W-P-E-T-Q-K-G-V-I-F-Y-E-S-H-G-K-L-E-Y-K-D-I-P | 91 ± 5 | 0 |
| [Y²] ALCOHOL DEHYDROGENASE I (1-24) (Yeast) S-Y-P-E-T-Q-K-G-V-I-F-Y-E-S-H-G-K-L-E-Y-K-D-I-P | 169 ± 8 | 0 |
| [V²] ALCOHOL DEHYDROGENASE I (1-24) (Yeast) S-V-P-E-T-Q-K-G-V-I-F-Y-E-S-H-G-K-L-E-Y-K-D-I-P | 123 ± 7 | 0 |

EXAMPLE 4

AAA1 Gene disruptions

A HindIII fragment was removed from the 3' end of the AAA1 gene, thereby deleting approximately 45% of the gene, and the 3.8 kb his-G-URA-3-hisG gene fragment was inserted into an EcoRV site (FIG. 2A). A DNA fragment containing the aaa1-1::hisG-URA3-hisG sequence was then transformed in a ura3/ura3 diploid yeast (Strain MGD502) (Table 4) (Ito et al., J. Bacteriol, 153:163-168 (1983)). These steps were done in the following manner.

Plasmid pBNH9 was constructed by deleting the 3' end of AAA1 from the HindIII site in the AAA1 insert to the HindIII site in the Bluescript (Stratagene) and the self-ligated. The 3.8 kb DNA fragment containing the yeast URA3 gene and two hisG repeat sequences was excised from the plasmid pNKY51 (Alani, E., et al., Genetics 116:541-545 (1987)) by digestion with BglII and BamHI, and its sticky ends were filled in by Klenow fragment. Plasmid pBNH9 was opened by cutting with EcoRV, and the 3.8 kb hisG-URA3-hisG containing fragment was blunt-end ligated into pBNH9 resulting in pBNHU9.

In order to study the biological significance of the N$^\alpha$-acetylation of proteins, a disruption deletion mutation was made by a single-step gene transplacement (Rothstein, R. J. *Met. Enzumol.* 101:202-211 (1983), which reference is incorporated herein by reference). Basically, a 4.9 kb DNA fragment was released from pBNHU9 by digestion with XhoI, and this fragment was used to transform various strains. Uracil prototrophs were selected.

Elimination of URA3 gene and one hisG repeat was carried out by patching Ura+, aaa− strain (AB18-a) onto 5-FOA (5-fluoro-orotic acid) plates, which are selective for ura3 strains (uracil plus 5-FOA), as described previously (Boeke, J. D., et al., *Mol. Gen. Genet.* 197:345-346 (1984)). Thereby, AB18-ap (aaa1::hisG. ura3), a 5-FOA resistant strain, was derived from AB18-a.

Ura+ transformants were isolated and sporulated, and the resulting asci were dissected into individual spores for tetrad analysis. Most diploid gave rise to four viable spores. However, each complete tetrad (20 tetrads) consisted of two wild-type-sized colonies and two small colonies. Characterization of complete tetrads indicated that large colonies were composed of ura− cells and that small colonies were formed by ura+ cells.

Tetrads were analyzed by DNA blot techniques. For these techniques, all restriction enzymes were purchased from New England Biolabs. DNA markers were obtained from Bethesda Research Laboratories. GeneScreen Plus membrane was from NEN. Yeast genomic DNA was isolated (Sherman, F., et al., *Methods in Yeast Genetics.* Cold Spring Harbor Laboratory, Cold Spring Harbor, NY (1986)), digested with restriction enzymes, electrophoresed on 0.8% agarose in Trisborate buffer, transferred onto GeneScreen Plus membrane, and hybridized with a random-primed, /BamHI fragment of AAA1 (derived from pBN9) for 24 hr, washed, and autoradiographed (Southern, E., *J. Mol. Biol.* 98:503-517 (1975)).

This DNA blot analysis of tetrads confirmed that uraspores contained the kb XhoI/BamHI or 2.5 kb XhoI/SphI fragment corresponding to the wild-type version of AAA1, while the ura+ spores contained the additional 3.8 kb URA3 gene fragment (FIG. 2B). Because haploid and diploid strains were viable when they contained only the aaa1-1::URA3 disruption, it is evident that AAA1 is not an essential gene. Further confirmation that URA3 marker now defines the aaa1 gene was obtained by N$^\alpha$-acetyltransferase enzyme assay (Lee, F.-J. S., et al. *J. Biol. Chem.* 263:14948-14955 (1988)).

Enzyme assay of protein extracts from cells confirmed that the ura+ spores contained no detectable N$^\alpha$-acetyltransferase activity, while the untransformed diploid (+/+), the heterozygous diploid (+/aaa1 1), and ura- spores has normal enzyme activity. A DNA fragment containing the aaa1::URA3 sequence was also transformed into ura3 haploid yeast strains (AB18, T3A,) (Table 4). ura− transformants of these haploid strains were isolated. DNA blot analysis and enzyme assay also confirmed that AAA1 gene was disrupted.

TABLE 4

| Strain | YEAST STRAINS Genotype[a] |
|---|---|
| MGD502 | MATa/MATα+/ade2, arg4/+, cyh$^r$/cyh$^s$, his3+, |

TABLE 4-continued

| Strain | YEAST STRAINS Genotype[a] |
|---|---|
|  | leu2/leu2 trp1/trp1, ura3/ura3 |
| MGD502-a | MATa/MATα+/ade2, arg4/+, cyh$^r$/cyh$^s$, his3+, leu2/leu2 trp1/trp1, ura3/ura3, aaa1-1/AAA1 |
| MGD502-2a | MATa/MATα+/ade2, arg4/+, cyh$^r$/cyh$^s$, his3+, leu2/leu2 trp1/trp1, ura3/ura3, aaa1-1/aaa1-1 |
| MGD502.4b | MATa, arg4, cyh$^r$, his3, leu2, trp1, ura3, AAA1 |
| MGD502.4a | MATa, arg4, cyh$^r$, his3, leu2, trp1, ura3, aaa1-1 |
| MGD502.4c | MATα ade2, cyh$^s$, leu2, trp1, ura3, AAA1 |
| MGD502.4d | MATα ade2, cyh$^s$, leu2, trp1, ura3, aaa1-1 |
| AB18 | MATa ade2-a, his5, lys2, trp1, ura3, aaa1-1 |
| AB18-ap | MATa ade2-1, his5, lys2, trp1, ura3, aaa1-2 |
| T3A | MATα his3, leu2, ura3, AAA1 |
| T3A-a | MATα his3, leu2, ura3, aaa1-1 |
| MS | MATa/MATα ade2-1/+, his5/his3, +/leu2, b lys2/+trp1/+, ura3/ura3 |
| MS-a | MATa/MATα ade2-1/+, his5/his3, +/leu2, c lys2/+trp1/+, ura3/ura3, aaa1-1/AAA1 |
| MS-2a | MATa/MATα ade2-1/+, his5/his3, +/leu2, d lys2/+trp1/+, ura3/ura3, aaa1-1/aaa1-1 |
| F676 | MATa ade2, his6, met1, sst1-3, ura1, rem1 |
| 3268-1-3 | MATα ade2, cry1, his4, lys2, sst2-1, trp1, tyr1, SUP4-3$^{ts}$ |

[a]aaa1-1 represents aaa1::hisG-URA-hisG; aaa1-2 represents aaa1::hisG, as described in Materials and Methods.
[b]Diploid from a cross of AB18 and T3A.
[c]Diploid from a cross of AB18-a and T3A.
[d]Diploid from a cross of AB18-a and T3A-a.

EXAMPLE 5

Phenotype of AAA1 Strains

The phenotype of the AAA1 strains was examined in the following manner. Colony morphology was examined by growing the tested strains in YPD medium at 30° C. for 3 d and then plating the cells on YPD plates. The size and morphology of colonies were evaluated after 5 d of growth.

Specific growth rates of tested strains were obtained by growing cells in the YPD medium at 30° C., 200 rpm, and OD$_{600}$ values were determined at specific time intervals.

Entry into stationary phase was determined by the following three methods: (i) determining the percentage of budded cells in 3 d old cultures grown in YPD medium, by mixing an aliquot of the culture with equal volume of 10% formaldehyde, sonicating briefly, and counting budded and unbudded cells with a hemocytometer (about 1000 cells per determination); (ii) determining the survival percentage in stationary phase (cells were maintained in SD medium at 30° C. for 5 d, and after dilution cells were plated on YPD plates, and after 2 d the number of colonies were counted); and (iii) glycogen accumulation was determined by inverting 5 d old culture plates over iodine crystals in a closed contained for 3 to 5 min and noting the appearance of dark brown colonies containing glycogen.

Sporulation was carried out as previously described (Sherman, F., et al., *Methods in Yeast Genetics.* Cold Spring Harbor Laboratory, Cold Spring Harbor, NY (1986)). Presporulation plates contained 0.5% Bacto-yeast, 0.5% Bacto-peptone, 1% glucose, and 2% Bacto-agar. Cells were grown on these plates for 1 d before transferring to sporulation plates, containing 1% potassium acetate, 0.1% Bacto-yeast extract, 2% Bacto-agar, and appropriate auxotrophic nutrients. Cells were grown at 30° C. unless otherwise indicated. Yeast transformation was by lithium acetate method (Ito, H., et al., *J. Bacteriol.* 153:163-168 (1983)). Standard techniques were used for diploid construction and tetrad dissection (Sherman, F., et al., *Methods in Yeast Genetics,* Cold Spring Harbor Laboratory, Cold Spring Harbor, NY (1986)). Plasmids were constructed by standard protocols as described by Maniatis et al. (Maniatis, T., et al., *Molecular Cloning: A Laboratory Manual.* Cold Spring Harbor Laboratory, Cold Spring Harbor, NY (1982)).

Sporulation efficiency was tested as follows: cells were grown on YPD plates, transferred to sporulation medium (1% potassium acetate, 0.1% Bacto-yeast extract, 0.05% dextrose) with appropriate auxotrophic nutrients and incubated at 25° C., 250 rpm for 1 d. Cells were harvested by centrifugation (1200 x g for 5 min at 20° C.), and resuspended in minimal sporulation medium (aqueous 1% potassium acetate) with appropriate auxotrophic nutrients and incubated 2 d. The percentage of sporulated cells was determined by counting >500 cells.

Heat sensitivity was determined by growing the cells to late log phase in YPD medium at 30° C., diluting to about $1 \times 10^5$ per ml in SD medium, and heat-shocking at 54° C. Aliquots were removed at the indicated times, chilled in an ice bath, and after dilution, cells were plated on a YPD plate. Three days later, colonies were counted, and survival percentages were determined.

EXAMPLE 6

Morphology of AAA1 Strains

The small colonies formed by ura⁻ cells from tetrad analysis provided genetic evidence that the slow-growing cells might have suffered the aaa1-1 disruption. The specific growth rate of each haploid cells (wild type and aaa1 mutant) was determined. The data clearly demonstrated that aaa1 mutants have a 40-60% decrease in their specific growth rate (Table 5).

In order to determine whether aaa1 mutation will affect the entrance of a cell into stationary phase, the ratio of budded cells, percentage of stationary survivals, and glycogen accumulation were examined. Cultures of each of eight strains (Table 5) were grown in YPD medium for 3-5 days at 30° C., until no more further increase in cell number was detected. Table 5 shows that cultures of aaa1 cells of either mating type exhibited ratios of budded to unbudded cells characteristic of exponentially growing cultures, whereas the wild-type strains had bud ratios characteristic of stationary phase cultures. In addition, multiple site and aberrant budding were frequently observed for the mutant cells. The survival percentage in stationary phase was determined by growing each of the eight strains in SD medium for 5 days at 30° C. This experiment revealed that the non-proliferating cultures of aaa1 strains lost viability more rapidly than did cultures of wild-type strains (Table 5). Glycogen accumulation was determined after plating each of eight strain onto YPD plate for 5 days. These nongrowing plates cultures were treated with brief exposure to iodine vapor. Only the wild-type turn dark brown due to accumulation of storage glycogen when cell enter stationary phase. The results presented above indicate that $N^\alpha$-acetyltransferase is required for cells to enter the stationary phase.

When 3 days old cultures were plated onto YPD plate, the aaa1 colonies were found to be varied in size and misshapen, and approximately 80% were observed to be smaller in size than the wilt-type cells. Multiple mutant colonies were picked up, grown in YPD for 3 days, and plated onto YPD plate. These aaa1 mutant colonies were also varied in size and misshapen.

TABLE 5

EFFECT OF AAA1 ON THE SPECIFIC GROWTH RATE AND ENTRY INTO STATIONARY PHASE

| Strain | Specific Growth Rate[a] ($hr^{-1}$) | Budded Cells[b] (%) | Survival in Stationary Phase[c] (%) | Glycogen Accumulation |
|---|---|---|---|---|
| MGD502.4b (AAA1) | 0.439 | 8 | 71 | + |
| MGD502.4a (aaa1-1) | 0.169 | 45 | 9 | − |
| MGD502.4c (AAA1) | 0.435 | 10 | 62 | + |
| MGD502.4d (aaa1-1) | 0.179 | 48 | 6 | − |
| AB18 (AAA1) | 0.421 | 7 | 56 | + |
| AB18-a (aaa1-1) | 0.172 | 46 | 6 | − |
| T3A (AAA1) | 0.496 | 10 | 73 | + |
| T3A-a (aaa1-1) | 0.302 | 54 | 10 | − |

[a]Cells were grown in the YPD medium at 30° C., 200 rpm and OD$_{600}$ was determined at various time intervals.
[b]Cells were grown in the YPD medium at 30° C. for 3 d. After brief sonication, budded and unbudded cells were counted with a hemocytometer. >1000 cells were counted for each determination.
[c]Strains were maintained in SD medium at 30° C. for 5 days. Cells were plate on a YPD plate, and colonies were counted after two days.

EXAMPLE 7

The AAA1 Gene is Required for Sporulation

Sporulation in yeast, initiated upon starvation of MATa/MATα diploid cells, represents a regulated program of differentiation (Esposito, R. E. et al., *In: The Molecular Biology of the Yeast Saccharomyces: Life Cycle and Inheritence* (Strathern, J. N. et al., Eds.) Cold Spring Harbor Laboratory, Cold Spring Harbor, NY (1981)).

In order to assess whether $N^\alpha$-acetylation plays a role in sporulation, two sets of genotype diploid yeast strains (MGD502 and MS) (see Table 4), representing wild type (+/+), heterozygous disrupted (+/aaa1-1), homozygous disrupted (aaa1-1/aaa1-1) diploid, were used. As shown in Table 5, both homozygous (aaa1-1/aaa1-1) diploid strains (MS-2a and MGD502-2a) did not sporulate efficiently.

EXAMPLE 8

AAA1 Gene is Required for a Specific Mating Type Functions

Mating experiments were performed in the following manner. Strains to be tested for mating were grown overnight in YPD medium. Equal numbers of cells from each mating type (about $5 \times 10^6$) were mixed, incubated in YPD medium for 6 hr at 30 C, and examined for agglutination. In addition, the cells were plated on SD plates, containing nutrients essential for auxotrophic selection, on which only diploids resulting from mating should grow. The individual mating type cells were also plated singly on SD plates to assay for the reversion of auxotrophic markers, and no prototrophs were observed.

For the a-factor assay, about $10^4$ cells of the tester strain 3268-1-3 (α ss2-11 were spread onto a YPD (pH 4.5) plate, and cells of the a-type strains to be tested were spotted on the plate. Zones of growth inhibition were clearly visible after 2-3 days of incubation at 30° C.

aaa1 mutants (MDG502.4a and AB18-a; both are a-mating type) were tested for α-factor response. Cells were grown overnight at 30° C. in YPD, washed, resuspended in 5 ml of YPD containing α-factor (1 μM) at a cell density of $1 \times 10^6$ cells per ml, and incubated at 30° C. Samples (0.1 ml) were removed at various intervals, mixed with an equal volume of 10% formaldehyde, and Gi phase arrested cells were determined by the ratio of budded to unbudded cells.

Haploid *S. cerevisiae* cells occur in two mating types, a and α, determined by the MAT locus (Nasymth, K., et al., *Science* 237:1162-1170 (1987)). Cells of opposite mating type can participate in a mating reaction that results in cell fusion and creation of a diploid cell (Bender, A., et al., *Genetics* 121:463-476 (1989); Sprague, G. F., et al., *Annu. Rev. Microbiol.* 37:623-660 (1983); Thorner, J., In: *The Molecular Biology of the Yeast Saccharomyces: Life Cycle and Inheritance*, Strathern, E. W., et al. (eds.), Cold Spring Harbor Laboratory, Cold Spring Harbor, NY, pp. 143-180 (1981)). Several proteins are responsible for the mating process, although it is unclear whether $N^\alpha$-acetylation of any of these occurs.

Matings were thus carried out by gently mixing with the aaa1 strains (MDG502.4d(α), MDG502.4a(a), T3A-a(α) or AB18-1(a)) with strains of opposite mating type. Surprisingly, the a-type aaa1 mutant strains (AB18-a and MDG502.4a) did not agglutinate as well as wild-type a-type cells when mixed with wild-type α-type cells. Quantitative mating tests indicated that mating efficiency of MATa aaa1 cells was significantly reduced, although not ablated (Table 7). Two α-type aaa1 mutants (T3A-a and MGD502.4d) produced α-factor at levels similar to the wild-type strains (T3A and MGD502.4c). However, two a-type aaa1 mutants (AB18-a and MGD502.4a) produced less a-factor than wild-type strains (AB18 and MGD502.4b). The a-type aaa1 mutant (MGD502.4a) produced at least 30-fold less a-factor than the wild-type (MGD502.4b). Similar results were also found for AB18-a in comparison to AB-18.

a-type cells are known to secrete the BAR1 gene product, so-called barrier activity, which degrades α-factor and thereby triggers the mating response (Hicks, J. B., et al., *Nature* 260:246-248 (1976); Kronstad, J. W., *Cell* 50:369-377 (1987); Manney, T. R., *J. Bacteriol.* 155:291-301 (1983); Sprague, G. F., Jr., et al., *Annu. Rev. Microbiol.* 37:623-660 (1983)).

Barrier activity was detected by interference in α-factor produced zones by a streak of a-mating type cells, as described by Sprague and Herskowitz (Sprague, G. F., Jr. et al., *J. Mol. Biol.* 153:305-321 (1981)) and by using F676 (sst1) as the tester strain, as described by Hicks and Herskowitz (Hicks, A. H., et al., *Proc. Natl. Acad. Sci. U.S.A.* 81:7021-7025 (1984)). Synthetic α-factor was purchased from the Bachem Bioscience Inc. and dissolved in 90% methanol (2 mg/ml).

This experiment revealed that a-type aaa1 mutant strains (AB18-a and MDG502.4a) had only a slight reduction of barrier activity in comparison to wild-type and supersensitive cells. In addition, a-type aaa1 mutants (AB18-a and MDG502.4a) fail to arrest in G1 phase, when the cells were resuspended in the YPD containing 1 μM α-factor.

EXAMPLE 9

Assay For Pheromone Production

The quantitative measurement of pheromone production was carried out as follows: cells were grown to late log phase at 30° C., 200 rpm, in YPD medium. Cells were pelleted twice by centrifugation at $1.3 \times 10^4$ g for 5 min before assaying the supernatant for pheromone activity. Serial dilutions (two- to four-fold) of pheromone-containing supernatants in citrate buffer (pH 4.5) were spotted (10 μl) onto a lawn of cells that are supersensitive to pheromones and incubated for 36-48 hr at 23° C.

EXAMPLE 10

Transcriptional Regulation of AAA1 Gene

Cells from 500 ml cultures were harvested at mid-log phase in YPG medium and at different stages of growth in YPD medium. Heat-shock was carried out as follows: when the $A_{600}$ of a YPD culture reached about 2.0, two 75 ml aliquots were removed; one was heated at 37° C. for 2 hr, and the other was incubated at 30° C. Total RNA was extracted from each sample (Sherman, F., et al., *Methods in Yeast Genetics*. Cold Spring Harbor Laboratory, Cold Spring Harbor, NY (1986)). Yeast RNA (10 μg) was electrophoresed on a 1.2% agarose/formaldehyde gel (Lehrach, H., et al., *Biochemistry* 16:4743-4751 (1977)). The lane containing the RNA markers was sliced out, visualized by staining with ethidium bromide, and used for determining the molecular sizes of the RNAs. The RNA was transferred onto GeneScreen Plus membrane and hybridized with random-primed, [$^{32}$P]-AAA1 (derived from pBH9, FIG. 2A) and β-tubulin (Neff, N. F., et al., *Cell* 33:211-219 (1983)) DNA for 24 hr, washed, and autoradiographed (Thomas, P. S., *Proc. Natl. Acad. Sci. USA* 77:5201-5205 (1980)). The levels of the mRNAs for the AAA1 and β-tubulin were determined.

Total RNA was thus prepared from cells grown in YPG medium at mid-log phase and YPD medium at early log phase, at mid-log phase, at stationary phase, and after heat-shock at 37° C. for 2 hr. RNA blot analysis was carried out with a random-primed, -radiolabeled AAA1 and yeast β-tubulin probes. There was no effect of glucose repression, growth phase, or heat-shock on the levels of transcription of the AAA1 in comparison to β-tubulin gene (Neff, N. F., et al., *Cell* 33:211-219 (1983)).

EXAMPLE 11

AAA1 MUTANTS ARE SENSITIVE TO HEAT SHOCK $N^\alpha$-acetylation has been suggested to play a role in protecting various proteins against intracellular proteolytic degradation (Jornvall, H., *J. Theor. Biol.* 55:1-12 (1975); Rubenstein, P., nt al., *J. Biol. Chem.* 254:11142-11147 (1979)). The rate of protein turnover mediated by the ubiquitin-dependent degradation system also has been documented to depend on the presence of a free α-NH$_2$ group at the N-terminus of model proteins (Bachmair, A., et al., *Science* 234:179-186 (1986)), and in yeast cells, polyubiquitin has been demonstrated to be a heat-shock protein (Finley, D., et al., *Cell* 48:1035-1046 (1987); Tanaka, K., et al., *EMBO J.* 7:495-502 (1988)). However, it has not been shown whether or not $N^\alpha$-acetylation of proteins plays a role in resistance to heat-shock. Therefore, exponentially growing cells in eight diploid strains (4 aaa1 mutants and 4 wild-type) were heat-shocked at 54° C., and the survival percentages were determined at various time points. As shown in FIG. 3, aaa1 strains (MGD502.4a and MGD502.4d) are more sensitive to heat-shock that wild-type strains (MGD502.4c and MGD502.4b). Other aaa1 strains (AB18-a and T3A-a) were also more sensitive than wild-type strains (AB18 and T3A).

EXAMPLE 12

Expression of AAA1 Gene can Complement the AAA1 Mutation

Expression plasmids for the AAA1 gene were constructed by inserting the AAA1 coding region into the pVT-L100 (containing a LEU2 marker) or pVT-U100 (containing a URA3 marker) expression vectors at the XbaI site immediately following the ADHI promoter (Vernet, T., et al., Gene 52:225–233 (1987)). These plasmids are identified as pLA1 or pUA1, respectively.

Various aaa1 mutants were transformed with plasmids pLA1 or pUA1, containing the AAA1 gene. The MDG502-2a/T transformant (containing pLA1) restored the sporulation deficiency found in MDG502-2a (Table 6). In addition, introduction of pLA1 into MDG502.4a (MATa, aaa1) and pUA1 into AB18-ap (MATa, aaa1-2), restored the mating efficiency (Table 7). These transformants also expressed a-mating factor as abundantly as weld-type. Moreover, the specific growth rate of these transformants was restored, and the cells were able to enter the stationary phase.

TABLE 6

EFFECT OF AAA1 ON THE SPORULATION EFFICIENCY[a]

| Strain | AAA1/Locus | Sporulation Efficiency (%) | Plasmid PLA1(AAA1−) |
|---|---|---|---|
| MGD502 | AAA1/AAA1 | 27 | − |
| MGD502-a | aaa1-1/AAA1 | 23 | − |
| MGD502-2a | aaa1-1/aaa1-1 | <0.1 | − |
| MGD502-2a/T[b] | aaa1-1/aaa1-1 | 21 | + |
| MS | AAA1/AAA1 | 16 | − |
| MS-a | aaa1-1/AAA1 | 12 | − |
| MS-2a | aaa1-1/aaa1-1 | <0.1 | − |

[a]Sporulation efficiency of each strain was determined after incubation in sporulation and minimal sporulation media at 25° C. for 3 d. as described in Materials and Methods.
[b]MGD502-2a/T is MGD502-2a transformed with pLA1 plasmid which expressing the AAA1 gene.

EXAMPLE 13

The AAA1 Gene of Yeast

Yeast strains lacking the $N^\alpha$-acetyltransferase gene, AAA1, grew as smaller, variably sized, and misshapen colonies in comparison to wild-type strains and that cells from these strains budded multiply and abnormally. In addition, AAA1 was demonstrated to be required for entrance into stationary phase, sporulation, resistance to heat-shock and a-specific mating type functions, although the role of $N^\alpha$-acetylation in these processes remains unclear.

Hershko et al. (Hershko, A., et al., Proc. Natl. Acad. Sci. USA 81:7021–7025 (1984)) showed that $N^\alpha$-acetylated proteins are degraded by the ATP-dependent, ubiquitin system less rapidly than proteins with free N-termini, and they suggested that $N^\alpha$-acetylation is involved in protection from protein degradation. In addition, induction of the UB14 gene (encoding ubiquitin) by heat-shock suggested that ubiquitin plays a role in the heat-shock response and that its physiological role may be to degrade altered or toxin proteins generated by environmental stress (Finley, D., et al., Cell 48:1035–1046 (1987); Tanaka, K., et al., EMBO J. 7:495–502 (1988)). We have demonstrated indirectly that $N^\alpha$-acetylation plays a role in resistance to heat-shock. However, how many $N^\alpha$-acetylated proteins are involved in protection from heat-shock and whether an exposed $\alpha$-NH$_2$ group in one or more of these proteins forms a recognition signal for ubiquitin conjugation and ubiquitin-mediated degradation is at present unknown.

Perhaps the most remarkable of the identified phenotypes of the aaa1 mutants is that a-type, but not α-type, aaa1 mutants mated less efficiently. It has been observed previously that mutations in STE2(α-factor receptor) (Harting, A., et al., Mol. Cell Biol. 6:2106–2114 (1986); Jenness, D. D., et al., Cell 35:521–529 (1983)), STE6 and STE16 (genes required for a-factor maturation) (Powers, S., et al., Cell 47:413–422 (1986); Wilson, K. L., et al., Mol. Cell Biol. 4:2420–2427 (1984)), MFa1 and MFa2 (a factor) (Michaelis, S., et al., Mol. Cell Biol. 8:1309–1318 (1988)) resulted in a million-fold reduction of mating type efficiency. In contrast, the aaa1 mutation resulted in a 1000-fold reduction of mating type efficiency. Thus, it is likely that the aaa1 mutation reduced, but did not abolish, the expression of certain a-specific gene products, as has been observed for the ard1 mutation (Whiteway, M., et al., Cell 43:483–492 (1985)). The ARD1 gene product has been suggested to act, directly or indirectly, at the HML locus and to repress its ex-

TABLE 7

MATING EFFICIENCIES OF WILD-TYPE AND AAA1 STRAINS[a]

| α strain | | a strain | | Mating Efficiency |
|---|---|---|---|---|
| Strain | Genotype | Strain | Genotype | (# of diploids) |
| MGD502.4c | α AAA1 | MGD502.4b | a AAA1 | 2.1 × 10$^5$ |
| MGD502.4c | α AAA1 | MGD502.4a | a aaa1-1 | <100 |
| MGD502.4d | α aaa1-1 | MGD502.4b | a AAA1 | 8.2 × 10$^4$ |
| MGD502.4d | α aaa1-1 | MGD502.4a | a aaa1-1 | <100 |
| T3A | α AAA1 | AB18 | a AAA1 | 1.4 × 10$^5$ |
| T3A | α AAA1 | AB18-a | a aaa1-1 | <100 |
| T3A-a | α aaa1-1 | AB18 | a AAA1 | 7.5 × 10$^4$ |
| T3A-a | α aaa1-1 | MGD502.4a/T[b] | a aaa1-1 pLA1(aaa1+) | 7.3 × 10$^4$ |
| T3A | α AAA1 | AB18-ap/T[c] | a aaa1-2 pUA1(AAA1+) | 6.7 × 10$^4$ |

[a]Mating efficiency was determined at 30° C. as described in Materials and Methods.
[b]MGD502.4a/T was MGD502.4a transformed with pLA1 carrying the AAA1 gene.
[c]AB18-ap/T was AB18-ap transformed with pUA1 carrying the AAA1 gene.

pression (Whiteway, M., et al., *Mol. Cell Biol.* 7:3713–3722 (1987)).

Different levels of acetylation have been observed for several eukaryotic proteins (Garlick, R. L., et al., *J. Biol. Chem.* 256:1727–731 (1981); Jornvall, H., *Eur. J. Biochem.* 72:443–452 (1977); MacLeod, A. R., et al., *Eur. J. Biochem.* 78:281–291 (1977); Mahoney, W. C., et al., Biochemistry 19:4436–4442 (1980); Smyth, D. G., et al., *Nature* 288:613–615 (1980); Stegink, L. D., et al., *J. Biol. Chem.* (1982)). Furthermore, isoenzymes (ADH I and ADH II) have also been shown to differ in their levels of acetylation (Jornvall, H., et al., *FEBS Lett.* 111:214–218 (980)). This differential acetylation may be due to differences in primary structure between the isozymes, a lack of available acetyl-CoA, or differences in level of enzyme activity. However, synthetic peptides mimicking residues 1-24 of both ADH isoenzymes were equally acetylated by the yeast $N^\alpha$-acetyltransferase, suggesting that under conditions where acetyl CoA is in excess that effective acetylation of both isoenzymes should proceed (Lee, F-J. S., et al., *J. Biol. Chem.* 263:14948–14955 (1988)). Furthermore, RNA blot analysis reveals that there was no major effect of glucose repression, different growth phase, or heat-shock on the transcriptional regulation of the AAA1 gene. However, these results do not rule out that $N^\alpha$-acetylation is not regulated by post-translational modification (phosphorylation or glycosylation) of or regulation (inhibition or activation) of $N^\alpha$-acetyltransferase.

The expanded usage of these aaa1 mutants and the AAA1 gene forms the basis for elucidating the biological function and the regulation of $N^\alpha$-acetylation in yeast.

EXAMPLE 14

The aaa1 Allele Alters Protein Synthesis in Saccharomyces Cerevisiae

It is not clear how $N^\alpha$-acetylation affects eukaryotic translation and processing (Wold, F., *Trends Biochem. Sci.* 9:256-257 (1984)) and protects against proteolytic degradation (Jornvall, H., *J. Theor. Biol.* 55:1–12 (1975); Rubenstein et al., *J. Biol. Chem.* 254:11142–11147 (1979)). Further, the rate of protein turnover mediated by the ubiquitin-dependent degradation system apparently depends on a free $\alpha$-$NH_2$ group at the $NH_2$-terminus of model proteins (Hershko et al., *Proc. Natl Acad. Sci. USA* 81:7021–7025 (1984); Bachmair et al., *Science* 234:179–186 (1986)), and this dependence indicates that $N^\alpha$-acetylation plays a crucial role in impeding protein turnover.

Serine and alanine are the most frequently observed N-terminal residues in acetylated proteins, and these residues, together with methionine, glycine, threonine, valine, and aspartic acid account for almost all $N^\alpha$-acetylated residues (Tsunasawa et al., *Methods Enzymol.* 106:165–170 984); Driessen et al., *CRC Crit. Rev. Biochem.* 18:281–325 (1985); Persson et al., *Eur. J. Biochem.* 152:523–527 (1985); Augen et al., *Trends Biochem. Sci.* 11:494–497 (1986); Tsunasawa et al., *J. Biol. Chem.* 260:5382–5391 (1985)). However, since not all proteins with these residues at the N-termini are acetylated, the basis by which certain proteins become acetylated remains unclear.

In order to study the effect of $N^\alpha$-acetyltransferase deficiency on protein synthesis in yeast, a comparison between the soluble proteins, isolated and then separated by two-dimensional gel electrophoresis, from wild type and aaa1 mutant was carried out by computer-based analysis of two-dimensional protein gels.

For this purpose, yeast strains T3A (MAT$\alpha$. his3, leu2, ura3, AAA1) and T3A-a (MAT$\alpha$, his3, leu2, ura3, aaa1-1) were used. Yeast culture media were prepared, as described by Sherman et al. (*Methods in Yeast Genetics* (Cold Spring Harbor Laboratory, Cold Spring Harbor, NY) (1986)): YPD contained 1% Bacto-yeast extract, 2% Bacto-peptone, and 2% glucose. YNB medium: succinate, 10.0 g/l; NaOH, 6.0 g/l; $(NH_4)_2SO_4$, 5.0 g/l; yeast nitrogen base (without amino acids and $(NH_4)_2SO_4$), 1.7 g/l; 18 amino acid (without methionine and cysteine), 12.5 mg/l each; adenine and uracil, 10 mg/l each; and glucose 20 g/l.

Yeast were grown overnight on a rotary shaker at 25° C., 200 rpm in YNB medium to $A_{660}=0.75$. Yeast proteins were labelled by adding ($^{35}S$)-methionine (~1200 Ci/mmol) to a 10 ml yeast culture at a concentration of 10 μCi/ml and shaken for another 20 min at 25° C. After adding ice to chill the culture, the cells were isolated by centrifugation (7000 x g) at 4° C. for 5 min in 15 ml Corex tubes, washed once with cold distilled water, and centrifuged. 300 μl of cold distilled water were added to the cell pellet, followed by the addition of 0.45 mm glass beads up to the meniscus. The cells were disrupted by vortexing vigorously for 30 sec (4 times) with chilling on ice for 1 in between each 30 sec burst. The homogenate was removed from the glass beads with an Eppendorf pipet and placed in a 1.5 ml microfuge tube. The glass beads were washed twice with 100 μl of distilled water, and the washes were added to the homogenate. 40 μl (1/10 vol) of a solution containing 0.3% SDS, 1.0% β-mercaptoethanol, 50 mM Tris-HCl, pH 8.0 was added. The solution was heated in the boiling water bath for 2 min and then cooled on ice. 50 μl of a solution containing 1 mg/ml DNase I, 500 μg/ml RNase A, 50 mM $MgCl_2$ in 50 mM Tris-HCl, pH 7.0 was added to the lysate, and the solution was incubated on ice for 10 min. The lysate was centrifuged in microfuge for 8 min, and the supernatant was transferred to a fresh tube and frozen in liquid nitrogen.

Pairs of two-dimensional gels were run for two different sample preparpations and computer-analyzed by Protein Databases Inc. (Huntington Station, NY). The gels were prepared according to the method of Garrels (Garrels, J. I., *J. Biol. Chem.* 264:5269–5282 (1989)). Lysates containing ~400,000 cpm were loaded onto each gel. The ampholine range of the isoelectric focusing (first dimension) was pH 4 to 7. The polyacrylamide concentratoin of the sodium dodecyl sulfate (second dimension) was 12.5%. The gels were processed for fluorography. Three sets of exposures were prepared for each sample in two experiments (3-, 6-, 12-day). The films were scanned with an Optronics P-1000 scanner interfaced to a PDP-11/60 computer. The data were transferred to a PDQuest workstation. The protein spots were identified, quantitated, and compared with the PDQuest system, which is based on the system of Garrels and Franza (Garrels et al., *J. Biol. Chem.* 264:5283–5298 (1989)).

The effects of $N^\alpha$-acetyltransferase deficiency on protein synthesis were thus examined by a comparison of the two-dimensional gel electrophoretic pattern of the soluble proteins from wild type and aaa1 mutant yeast cells. 855 discrete protein spots were detected by computer analysis of the gels. Without a change in their molecular mass, 48 proteins, identified in wild type cells, were observed to have higher pI values in the aaa1 mutant cells. Such shifts to higher pI's likely result from protonation of the α-NH$_2$ group in proteins, lacking an acetyl group. In addition, the aaa1 mutant cells contained 144 fewer proteins than the wild type cells.

Hershko et al. (Hershko et al., *Proc. Natl. Acad. Sci. USA* 81:7021–7025 (1984)) showed that N$^\alpha$-acetylated proteins are degraded by the ubiquitin/ATP-dependent system less rapidly than proteins with a free N-terminus and suggested that N$^\alpha$-acetylation may prevent degradation by this system. It is possible that the 144 proteins no longer detected in the aaa1 mutant may have been degraded by this pathway. However, most of the "shifted" proteins were not more labile. Hence, N$^\alpha$-acetylation cannot be the only factor involved in preventing protein degradation.

27 new proteins appeared in aaa1 mutant. The synthesis of these proteins results from derepression or activation of genes regulated by regulatory proteins, which are no longer acetylated. Such a hypothesis had been suggested to be the case for a protein regulating a-specific mating type genes in the aaa1 mutant (Mullen et al., *EMBO J.* 8:2067–2075 (1989)).

Furthermore, a comparison between the proteins of wild type and aaa1 mutant revealed that 71 proteins of aaa1 mutant were decreased by >50% and 34 proteins were increased by >200%. Such diminished or enhanced synthesis might also be controlled by regulatory proteins lacking N$^\alpha$-acetylation.

The experiments revealed that only 20% of the soluble proteins were either shifted or disappeared in the aaa1 mutant (i.e., indicating that they probably lacked a N$^\alpha$-acetyl group), although it has been suggested that 50% of the soluble proteins in yeast are N$^\alpha$-acetylated (Brown, J. L., *Int. Congr. Biochem. Abstr.,* Vol. 11, International Union of Biochemistry, Canada, pp. 90 (1979)). The presence of additional N$^\alpha$-acetyltransferases may account for this apparent difference.

N$^\alpha$-acetylation is a common and important chemical modification of eukaryotic proteins, as indicated by the large number of proteins whose synthesis is altered by deleting the N$^\alpha$-acetyltransferase gene.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A prokaryotic or eukaryotic cell which expresses an altered AAA1-encoded N$^\alpha$-acetyltransferase.

2. The cell of claim 1 which is a yeast cell.

3. The yeast cell of claim 2 which substantially lacks N$^\alpha$-acetyltransferase activity.

4. The yeast cell of claim 3 which contains as aaa1-1 or an aaa1-2 allele of the AAA1 gene.

5. A recombinant molecule containing an altered AAA1 gene, wherein said recombinant molecule is DNA or cDNA.

6. The cell of claim 1, wherein said cell is a bacterial cell.

7. The cell of claim 1, wherein said cell is a yeast, plant or mammalian cell.

8. A method for producing a peptide lacking an N$^\alpha$-acetylated amino terminus which comprises expressing said peptide in a yeast cell having an AAA1 gene, wherein said gene contains a mutation resulting in the substantial loss of AAA1 gene product activity, and renders said cell unable to catalyze said N$^\alpha$-acetylation of said peptide.

* * * * *